US011839432B2

(12) United States Patent
Crowther et al.

(10) Patent No.: US 11,839,432 B2
(45) Date of Patent: *Dec. 12, 2023

(54) VIRTUAL REALITY SURGICAL TRAINING SYSTEMS

(71) Applicant: FVRVS Limited, London (GB)

(72) Inventors: Ian Hew Crowther, Edgware (GB); Victoria Jane Smalley, Amersham (GB)

(73) Assignee: FVRVS Limited, London (GB)

( * ) Notice: Subject to any disclaimer, the term of this patent is extended or adjusted under 35 U.S.C. 154(b) by 21 days.

This patent is subject to a terminal disclaimer.

(21) Appl. No.: 17/592,775

(22) Filed: Feb. 4, 2022

(65) Prior Publication Data

US 2022/0151700 A1 May 19, 2022

Related U.S. Application Data

(63) Continuation of application No. 17/186,654, filed on Feb. 26, 2021, now Pat. No. 11,272,988, which is a
(Continued)

(51) Int. Cl.
*A61B 34/10* (2016.01)
*G06F 3/01* (2006.01)
(Continued)

(52) U.S. Cl.
CPC .............. *A61B 34/10* (2016.02); *G06F 3/011* (2013.01); *G06F 3/016* (2013.01); *G06T 15/005* (2013.01);
(Continued)

(58) Field of Classification Search
CPC ... A61B 34/10; A61B 2090/365; G06F 3/016; G06T 15/005; G06T 15/04; G06T 15/08; G06T 17/20; G06T 19/006; G06T 2210/41
See application file for complete search history.

(56) References Cited

U.S. PATENT DOCUMENTS 5,696,892 A 12/1997 Redmann et al.
7,626,589 B2 * 12/2009 Berger .................. G06F 3/1446
345/428
(Continued)

FOREIGN PATENT DOCUMENTS

EP 2387760 A1 11/2011
EP 3966667 A1 3/2022
(Continued)

OTHER PUBLICATIONS

Bernardi et al., Texture Atlasing: An Inside Look at Optimizing 3D Worlds! (2018).
(Continued)

*Primary Examiner* — Sing-Wai Wu
(74) *Attorney, Agent, or Firm* — Brown Rudnick LLP; Adam M. Schoen

(57) ABSTRACT

Disclosed herein are systems, methods, and software for providing a virtual environment with enhanced visual textures and haptic detail. In some embodiments, a texture atlas and UV mapping is used to render virtual objects having multiple textures that can be manipulated in real time. In some cases, UV coordinates are used to provide enhanced haptic detail.

16 Claims, 15 Drawing Sheets

Related U.S. Application Data continuation of application No. PCT/IB2020/000363, filed on May 8, 2020, which is a continuation-in-part of application No. 16/409,404, filed on May 10, 2019, now abandoned.

(51) Int. Cl.

| | |
|---|---|
| *G06T 15/00* | (2011.01) |
| *G06T 15/04* | (2011.01) |
| *G06T 15/08* | (2011.01) |
| *G06T 17/20* | (2006.01) |
| *A61B 90/00* | (2016.01) |
| *G06T 19/00* | (2011.01) |

(52) U.S. Cl.
CPC .............. *G06T 15/04* (2013.01); *G06T 15/08* (2013.01); *G06T 17/20* (2013.01); *A61B 2034/102* (2016.02); *A61B 2034/105* (2016.02); *A61B 2090/365* (2016.02); *G06T 19/006* (2013.01); *G06T 2210/41* (2013.01)

(56) References Cited

U.S. PATENT DOCUMENTS

| | | | |
|---|---|---|---|
| 7,889,205 | B1 | 2/2011 | Parenteau et al. |
| 11,272,988 | B2 | 2/2022 | Crowther et al. |
| 2008/0020362 | A1 | 1/2008 | Cotin et al. |
| 2009/0018808 | A1 | 1/2009 | Bronstein et al. |
| 2009/0160869 | A1 | 6/2009 | Smelyanskiy et al. |
| 2009/0177452 | A1 | 7/2009 | Ullrich et al. |
| 2013/0044927 | A1 | 2/2013 | Poole |
| 2013/0249912 | A1 | 9/2013 | Schmidt |
| 2014/0028693 | A1 | 1/2014 | Wang et al. |
| 2014/0172377 | A1 | 6/2014 | Taubin et al. |
| 2014/0272866 | A1 | 9/2014 | Kim |
| 2017/0004647 | A1 | 1/2017 | Grossman |
| 2017/0098055 | A1 | 4/2017 | Voth |
| 2017/0217103 | A1 | 8/2017 | Babaei et al. |
| 2019/0096119 | A1 | 3/2019 | Petkov et al. |
| 2019/0114822 | A1 | 4/2019 | Cernigliaro et al. |
| 2019/0251755 | A1 | 8/2019 | Douglas et al. |
| 2020/0357176 | A1 | 11/2020 | Crowther et al. |

FOREIGN PATENT DOCUMENTS

| | | |
|---|---|---|
| WO | WO-2010083272 A1 | 7/2010 |
| WO | WO-2015084837 A1 | 6/2015 |
| WO | WO-2015092361 A1 | 6/2015 |
| WO | WO-2020229890 A1 | 11/2020 |

OTHER PUBLICATIONS

PCT/IB2020/000363 International Preliminary Report on Patentability dated Nov. 16, 2021.
PCT/IB2020/000363 International Search Report and Written Opinion dated Sep. 30, 2020.
U.S. Appl. No. 16/409,404 Non-Final Office Action dated Oct. 16, 2020.
U.S. Appl. No. 17/186,654 Final Office Action dated Jul. 20, 2021.
U.S. Appl. No. 17/186,654 Non-Final Office Action dated May 5, 2021.
U.S. Appl. No. 16/409,404 Final Office Action dated Mar. 20, 2020.
U.S. Appl. No. 16/409,404 Office Action dated Dec. 2, 2019.
U.S. Appl. No. 16/409,404 Office Action dated Jan. 28, 2021.
U.S. Appl. No. 16/409,404 Restriction Requirement dated Sep. 9, 2019. .

\* cited by examiner

VIRTUAL REALITY SURGICAL TRAINING SYSTEMS

CROSS-REFERENCE

This application is a continuation of Ser. No. 17/186,654, filed Feb. 26, 2021, which is a continuation of International Patent Application No. PCT/IB2020/000363, filed May 8, 2020, which is a continuation-in-part of Ser. No. 16/409,404, filed May 10, 2019, which is incorporated herein by reference in its entirety.

BACKGROUND

Medical training and especially surgical training involves a great deal of hands-on learning, wherein student-healthcare providers (as well as experienced healthcare providers learning new skills) are able to practice and develop skills that they need in order become proficient at medical and surgical procedures in a hands-on and immersive training environment.

SUMMARY

Described herein are systems, software, and methods for providing medical training in a virtual, augmented, or mixed reality environment. In some embodiments, a system as described herein includes a virtual reality interface configured to provide a virtual, augmented or mixed reality experience for a user (including, in some embodiments, one or more of visual, auditory, and/or tactile stimulus). In some embodiments, a system further includes at least one hand-held component used by a user to interact with an object viewed within the virtual (or augmented or mixed) reality environment. In some embodiments, a hand-held component transmits a haptic feedback sensed by the user through the hand-held component.

Traditional medical and surgical training involve supervised direct patient interactions for healthcare providers in-training. Often times, it is the case that such training is insufficient to fully train healthcare provider in-training with respect to the procedures that they need to become facile with. This is especially the case with traditional surgical training wherein surgeons in-training are not always provided with sufficient hands-on experience in the operating room to become entirely facile with certain procedures. There is, therefore, a need to provide surgeons in-training with sufficient opportunities to have hand-on and realistic experience with surgical procedures.

To the extent that it has been possible to provide healthcare providers in-training with training modalities that utilize computer implemented methods, these methods are typically limited by current processing limitations that do not enable providing users with seamless realistic immersive training.

In contrast to traditional medical and surgical training techniques, described herein is a virtual (or augmented or mixed) reality training modality that provides a seamless virtual (or augmented or mixed) reality realistic operating room experience wherein a user is able to engage in a fully realistic computer simulated surgery.

The systems, software and methods described herein are configured to overcome limitations on existing computer implemented medical training technologies by storing data related to the virtual (or augmented or mixed) experience in a highly efficient manner that allows for calling of the information quickly without overly straining processor power. In general, realistic virtual (or augmented or mixed) experiences require processing a relatively large amount of data relatively quickly and the systems, software and methods described herein are configured to create a realistic training experience by providing an experience that includes a great deal of visual, and/or auditory, and/or tactile detail (e.g. data) that is presented seamlessly (e.g. without processing delay) to the user. For example, unused UV coordinates can be repurposed to refer to a texture atlas comprising various material types, thereby providing an efficient and streamlined method of applying textures to a virtual object in real-time. This provides a solution to the technical problem of generating a virtual environment with virtual objects that have multiple textures in real-time. Enhanced haptic detail can also be provided through the application of bump mapping to the haptic render engine. While bump mapping is conventionally applied to the visual render engine, it has never been integrated into the haptic render engine pipeline. Therefore, both the visual and haptic rendering methods described herein represent improvements in the technical field of virtual simulations that incorporates unconventional data processing steps. These methods are practically integrated into virtual simulations to provide an improved and realistic experience such as, for example, in training surgical techniques.

Described herein is a system for providing a virtual reality or augmented reality surgical simulation comprising a plurality of voxels, said system comprising a processor; a hand-held component operatively coupled to the processor; and a non-transitory computer readable storage medium encoded with a computer program that causes the processor to: identify at least one UV coordinate associated with a voxel of the plurality of voxels; locate data associated with the voxel within an atlas, wherein the data is located within the atlas using an offset value that is based on the at least one UV coordinate associated with the voxel; map the data onto the voxel; and display the data within the surgical simulation. In some embodiments, the hand-held component comprises a wand, a joystick, a mouse, a roller, a grasper, or a glove, wherein the hand-held component controls a virtual surgical instrument within the virtual or augmented reality surgical simulation, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, the computer program further causes the processor to display a movement of the virtual surgical instrument in the surgical field in the same direction as a movement of the hand-held component based on the input. In some embodiments, the virtual reality or augmented reality surgical simulation comprises a representation of at least one of a bone, a muscle, an organ, a blood vessel, blood, and a nerve. In some embodiments, the data comprises texture information associated with the voxel or haptic information associated with the voxel. In some embodiments, all textures that are applied within the surgical simulation are positioned on the atlas and each texture is associated with a set of unique UV coordinates. In some embodiments, the data comprises a texture computer program further causes the processor to display a seamless movement of the texture within the virtual reality or augmented reality surgical simulation. In some embodiments, the computer program further causes the processor to display both an exterior texture and an interior texture of a virtual object when that virtual object is cut with a virtual surgical instrument within the surgical simulation, and wherein the exterior texture and the interior texture are positioned on a single atlas and each have a unique location within the single atlas associated with unique UV coordinates. In some embodiments, the computer program further causes the processor to simultaneously display the exterior texture and the interior texture and wherein the processor draws upon the single atlas once. In some embodiments, the data comprises haptic information and the computer program further causes the processor to provide a haptic feedback to the user through the hand-held component. In some embodiments, the haptic feedback corresponds to bump map data. In some embodiments, when a force is transmitted to an object of interest within the virtual reality or augmented reality surgical simulation through the hand-held controller, the computer program further causes the processor to display a response of a texture associated with the virtual object to the force. In some embodiments, the haptic feedback comprises a sensation that represents the response of the texture to the force.

Described herein is computer implemented method comprising: locating a texture from a plurality of textures positioned on a single atlas, wherein the texture is located using an offset value that is based on at least one UV coordinate; mapping the texture onto a virtual object; displaying the virtual object as part of a virtual surgical field; receiving an input from a hand-held component when a user moves the hand-held component; and displaying an interaction in the virtual surgical field between a virtual surgical instrument and the virtual object based on the input. In some embodiments, the hand-held component comprises a wand or a joystick. In some embodiments, the hand-held component comprises a mouse or a roller. In some embodiments, the hand-held component comprises a surgical grasper or a glove. In some embodiments, the virtual object comprises a representation of at least one of a bone, a muscle, an organ, a blood vessel, blood, and a nerve. In some embodiments, all of the textures for virtual objects simulated by a voxel representation within the surgical field are positioned on the single atlas and each texture of all of the textures is associated with a set of unique UV coordinates. In some embodiments, the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, the method comprises displaying a movement of the virtual surgical instrument in the surgical field in the same direction as a movement of the hand-held component based on the input. In some embodiments, the interaction comprises moving the virtual object with the virtual surgical instrument and the method further comprises displaying a seamless movement of the texture along with the movement of the virtual object. In some embodiments, the interaction comprises cutting the virtual object and the method further comprises displaying an interior texture of the virtual object that is different than the texture, and wherein the interior texture is positioned on the single atlas and has a unique set of UV coordinates. In some embodiments, the method comprises displaying the texture and the inner texture and wherein a single draw call is made to the single atlas to render the texture and the inner texture. In some embodiments, the method comprises providing a haptic feedback to the user through the hand-held component. In some embodiments, the haptic feedback corresponds to bump map data. In some embodiments, the interaction comprises applying a force to the virtual object with the virtual surgical instrument and the method further comprises displaying a response of the texture to the force. In some embodiments, the force corresponds to a gripping of the virtual object with the virtual surgical instrument. In some embodiments, the haptic feedback comprises a sensation that represents the response of the texture to the force. In some embodiments, the interaction is displayed seamlessly during the period that the interaction is displayed.

In another aspect, disclosed herein is a computer based surgical training system, comprising: (a) a processor; (b) a hand-held component operatively coupled to the processor; (c) a non-transitory computer readable storage medium encoded with a computer program that causes the processor to: (i) locate data associated with a voxel within a virtual reality or augmented reality surgical simulation from within a texture atlas, wherein the data is located using an offset value that is based on at least one UV coordinate associated with the voxel; and (ii) map the data onto the voxel; wherein the data comprises a haptic data associated with a haptic signal transmitted through the hand-held component. In some embodiments, the hand-held component comprises a wand or a joystick. In some embodiments, the hand-held component comprises a mouse or a roller. In some embodiments, the hand-held component comprises a grasper or a glove. In some embodiments, the virtual reality or augmented reality surgical simulation comprises a representation of at least one of a bone, a muscle, an organ, a blood vessel, blood, and a nerve. In some embodiments, the haptic data used for a virtual object represented by voxels within the virtual reality or augmented reality surgical simulation are positioned on the texture atlas and each texture of the textures is associated with a set of unique UV coordinates. In some embodiments, the hand-held component controls a virtual surgical instrument within the virtual or augmented reality surgical simulation, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, the computer program further causes the processor to display a movement of the virtual surgical instrument in the simulation in the same direction as a movement of the hand-held component based on the input. In some embodiments, the computer program further causes the processor to transmit the haptic signal through the hand-held controller when the virtual surgical instrument contacts the voxel. In some embodiments, when a force is transmitted to a virtual object within the virtual reality or augmented reality surgical simulation through the hand-held controller, the computer program further causes the processor to transmit a haptic signal through the hand-held controller that is related to the force. In some embodiments, the force corresponds to a gripping of the virtual object with the virtual surgical instrument.

In another aspect, disclosed herein is a computer implemented method comprising: (a) locating haptic data from a plurality of haptic data positioned on a single atlas, wherein the haptic data is located using an offset value that is based on at least one UV coordinate; (b) mapping the haptic data onto a virtual object within a virtual surgical field; (c) receiving an input, from a hand-held component, corresponding to a movement of a virtual surgical instrument with the virtual surgical field when a user moves the hand-held component; and (d) transmitting a haptic signal through the hand-held component when the virtual surgical instrument interacts with the virtual object within the virtual surgical field. In some embodiments, the hand-held component comprises a wand or a joystick. In some embodiments, the hand-held component comprises a mouse or a roller. In some embodiments, the hand-held component comprises a surgical grasper or a glove. In some embodiments, the virtual object comprises a representation of at least one of a bone, a muscle, an organ, a blood vessel, blood, and a nerve. In some embodiments, the haptic data for a virtual object that is represented by voxels within the surgical field is positioned on the texture atlas and each of the haptic data is associated with a set of unique UV coordinates. In some embodiments, the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, the method comprises displaying a movement of the virtual surgical instrument in the surgical field in the same direction as a movement of the hand-held component based on the input. In some embodiments, when a force is applied to the virtual object with the virtual surgical instrument using the hand-held component the haptic signal is related to the force. In some embodiments, the force corresponds to a gripping of the virtual object with the virtual surgical instrument. In some embodiments, the haptic feedback comprises a sensation that represents the response of the virtual object to the force.

Described herein is a system for providing a virtual reality or augmented reality surgical simulation comprising a virtual object comprising a plurality of voxels, said system comprising: (a) a processor; (b) a hand-held component operatively coupled to the processor; and (c) a non-transitory computer readable storage medium encoded with a computer program that causes the processor to: (i) identify a plurality of UV coordinates associated with the plurality of voxels of the virtual object; (ii) locate data comprising a plurality of textures associated with the plurality of voxels of the virtual object within a texture atlas, wherein each of the plurality of textures is located within the texture atlas using an offset value that is based on at least one UV coordinate associated with at least one voxel of the plurality of voxels; (iii) map the data comprising the plurality of textures onto the plurality of voxels of the virtual object; and (iv) display the virtual object comprising the plurality of textures mapped onto the plurality of voxels within the surgical simulation. In some embodiments, the hand-held component comprises a wand, a joystick, a mouse, a roller, a grasper, or a glove, wherein the hand-held component controls a virtual surgical instrument within the virtual or augmented reality surgical simulation, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, the computer program further causes the processor to display a movement of the virtual surgical instrument in the surgical field in the same direction as a movement of the hand-held component based on the input. In some embodiments, the virtual reality or augmented reality surgical simulation comprises a representation of at least one of a bone, a muscle, an organ, a blood vessel, blood, and a nerve. In some embodiments, the data further comprises haptic information associated with the plurality of voxels. In some embodiments, all textures that are mapped within the surgical simulation are positioned on the texture atlas and each mapped texture is associated with a set of unique UV coordinates. In some embodiments, the data comprises a texture computer program further causes the processor to display a seamless movement of the texture within the virtual reality or augmented reality surgical simulation. In some embodiments, the computer program further causes the processor to display both an exterior texture and an interior texture of a virtual object when that virtual object is cut or altered to expose the interior texture with a virtual surgical instrument within the surgical simulation, and wherein the exterior texture and the interior texture are positioned on the texture atlas and each have a unique location within the texture atlas associated with unique UV coordinates. In some embodiments, the computer program further causes the processor to simultaneously display the exterior texture and the interior texture and wherein the processor draws upon the texture atlas once. In some embodiments, the data comprises haptic information and the computer program further causes the processor to provide a haptic feedback to the user through the hand-held component. In some embodiments, the haptic feedback corresponds to bump map data. In some embodiments, when a force is transmitted to an object of interest within the virtual reality or augmented reality surgical simulation through the hand-held controller, the computer program further causes the processor to display a response of a texture associated with the virtual object to the force. In some embodiments, the haptic feedback comprises a sensation that represents the response of the texture to the force.

Described herein is a computer implemented method comprising: (a) identifying a plurality of UV coordinates associated with a plurality of voxels of the virtual object; (b) locating data comprising a plurality of textures associated with the plurality of voxels of the virtual object within a texture atlas, wherein each of the plurality of textures is located within the texture atlas using an offset value that is based on at least one UV coordinate associated with at least one voxel of the plurality of voxels; (c) mapping the data comprising the plurality of textures onto the plurality of voxels of the virtual object; (d) receiving an input from a hand-held component when a user moves the hand-held component; and (e) display the virtual object comprising the plurality of textures mapped onto the plurality of voxels within the surgical simulation. In some embodiments, the hand-held component comprises a wand, a joystick, a mouse, a roller, a grasper, or a glove, wherein the hand-held component controls a virtual surgical instrument within the virtual or augmented reality surgical simulation, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, method further comprises displaying a movement of the virtual surgical instrument in the surgical field in the same direction as a movement of the hand-held component based on the input. In some embodiments, the virtual reality or augmented reality surgical simulation comprises a representation of at least one of a bone, a muscle, an organ, a blood vessel, blood, and a nerve. In some embodiments, the data further comprises haptic information associated with the plurality of voxels. In some embodiments, all textures that are mapped within the surgical simulation are positioned on the texture atlas and each mapped texture is associated with a set of unique UV coordinates. In some embodiments, the data comprises a texture computer program further causes the processor to display a seamless movement of the texture within the virtual reality or augmented reality surgical simulation. In some embodiments, the method further comprises displaying both an exterior texture and an interior texture of a virtual object when that virtual object is cut or altered to expose the interior texture with a virtual surgical instrument within the surgical simulation, and wherein the exterior texture and the interior texture are positioned on the texture atlas and each have a unique location within the texture atlas associated with unique UV coordinates. In some embodiments, the method further comprises simultaneously displaying the exterior texture and the interior texture and wherein the processor draws upon the texture atlas once. In some embodiments, the data comprises haptic information and the method further comprises providing a haptic feedback to the user through the hand-held component. In some embodiments, the haptic feedback corresponds to bump map data. In some embodiments, when a force is transmitted to an object of interest within the virtual reality or augmented reality surgical simulation through the hand-held controller, the computer program further causes the processor to display a response of a texture associated with the virtual object to the force. In some embodiments, the haptic feedback comprises a sensation that represents the response of the texture to the force.

Described herein is a system for providing a virtual reality or augmented reality surgical simulation comprising a virtual object comprising a plurality of voxels, said system comprising: (a) a processor; (b) a hand-held component operatively coupled to the processor; and (c) a non-transitory computer readable storage medium encoded with a computer program that causes the processor to: (i) receive an input from the hand-held component when a user moves the hand-held component, wherein said input comprises an interaction between a virtual surgical instrument and a surface of a virtual object; (ii) locate data comprising texture information associated with a location on the surface of the virtual object that engages in the interaction; (iii) determine a haptic value based on the texture information associated with the location on the surface of the virtual object that engages in the interaction; and (iv) provide haptic feedback for the interaction between the virtual surgical instrument and the surface of the virtual object through the hand-held component. In some embodiments, the hand-held component comprises a wand, a joystick, a mouse, a roller, a grasper, or a glove, wherein the hand-held component controls a virtual surgical instrument within the virtual or augmented reality surgical simulation, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, the computer program further causes the processor to display a movement of the virtual surgical instrument in the surgical field in the same direction as a movement of the hand-held component based on the input. In some embodiments, the virtual reality or augmented reality surgical simulation comprises a representation of at least one of a bone, a muscle, an organ, a blood vessel, blood, and a nerve. In some embodiments, the data further comprises texture information associated with the virtual object. In some embodiments, all textures that are mapped within the surgical simulation are positioned on a texture atlas and each mapped texture is associated with a set of unique UV coordinates. In some embodiments, the data comprises a texture computer program further causes the processor to display a seamless movement of the texture within the virtual reality or augmented reality surgical simulation. In some embodiments, the computer program further causes the processor to display both an exterior texture and an interior texture of a virtual object when that virtual object is cut or altered to expose the interior texture with a virtual surgical instrument within the surgical simulation, and wherein the exterior texture and the interior texture are positioned on the texture atlas and each have a unique location within the texture atlas associated with unique UV coordinates. In some embodiments, the computer program further causes the processor to simultaneously display the exterior texture and the interior texture and wherein the processor draws upon the texture atlas once. In some embodiments, the data comprises bump map data. In some embodiments, when a force is transmitted to an object of interest within the virtual reality or augmented reality surgical simulation through the hand-held controller, the computer program further causes the processor to display a response of a texture associated with the virtual object to the force. In some embodiments, the haptic feedback comprises a sensation that represents the response of the texture to the force.

Described herein is a computer implemented method comprising: (a) receiving an input from a hand-held component when a user moves a hand-held component, wherein said input comprises an interaction between a virtual surgical instrument and a surface of a virtual object within a virtual reality or augmented reality surgical simulation; (b) locating data comprising texture information associated with a location on the surface of the virtual object that engages in the interaction; (c) determining a haptic value based on the texture information associated with the location on the surface of the virtual object that engages in the interaction; and (d) providing haptic feedback for the interaction between the virtual surgical instrument and the surface of the virtual object through the hand-held component. In some embodiments, the hand-held component comprises a wand, a joystick, a mouse, a roller, a grasper, or a glove, wherein the hand-held component controls a virtual surgical instrument within the virtual or augmented reality surgical simulation, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, method further comprises displaying a movement of the virtual surgical instrument in the surgical field in the same direction as a movement of the hand-held component based on the input. In some embodiments, the virtual reality or augmented reality surgical simulation comprises a representation of at least one of a bone, a muscle, an organ, a blood vessel, blood, and a nerve. In some embodiments, the data further comprises texture information associated with the virtual object. In some embodiments, all textures that are mapped within the surgical simulation are positioned on the texture atlas and each mapped texture is associated with a set of unique UV coordinates. In some embodiments, the data comprises a texture computer program that further causes the processor to display a seamless movement of the texture within the virtual reality or augmented reality surgical simulation. In some embodiments, the method further comprises displaying both an exterior texture and an interior texture of a virtual object when that virtual object is cut or altered to expose the interior texture with a virtual surgical instrument within the surgical simulation, and wherein the exterior texture and the interior texture are positioned on the texture atlas and each have a unique location within the texture atlas associated with unique UV coordinates. In some embodiments, the method further comprises simultaneously displaying the exterior texture and the interior texture and wherein the processor draws upon the texture atlas once. In some embodiments, the data comprises bump map data. In some embodiments, when a force is transmitted to an object of interest within the virtual reality or augmented reality surgical simulation through the hand-held controller, the computer program further causes the processor to display a response of a texture associated with the virtual object to the force. In some embodiments, the haptic feedback comprises a sensation that represents the response of the texture to the force.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7A illustrates a computer simulated object having faces colored to show normal based blending. FIG. 7B illustrates computer simulated object having faces textured with single bone texture.

FIG. 11A illustrates a standard appearance of a haptic object without high frequency haptic surface data. FIG. 11B illustrates an enhanced appearance of surface detail on a haptic object due to application of high frequency haptic surface data by a visual rendering technique from the present disclosure.

DETAILED DESCRIPTION

Figure 1:
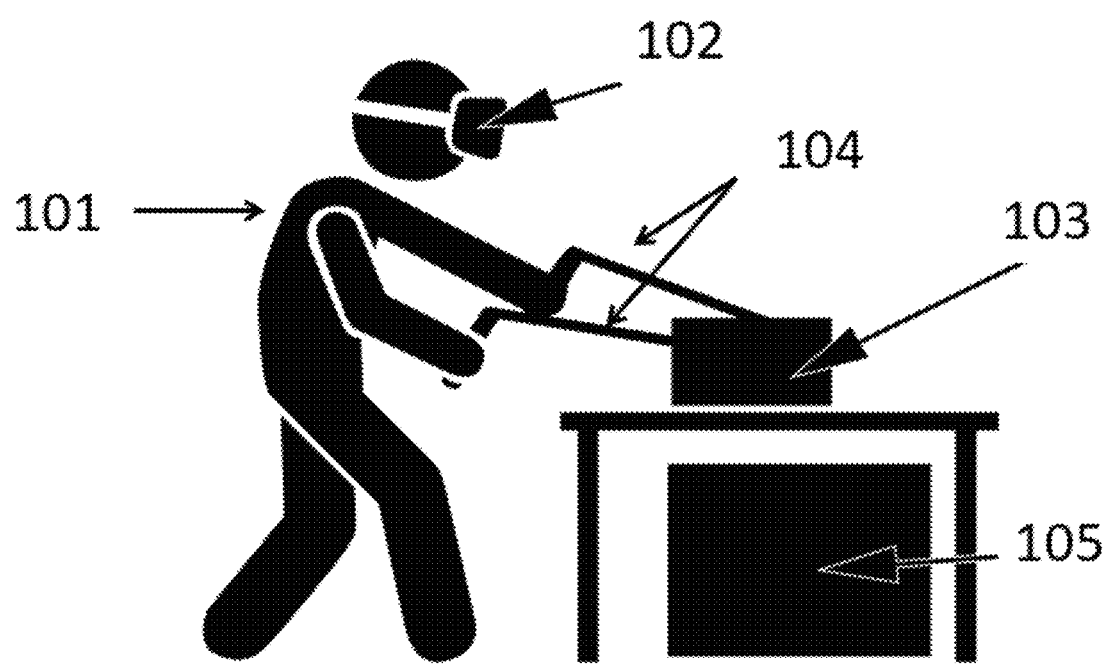
FIG. 1 illustrates an example of a user engaging a system disclosed herein.

Described herein are virtual reality surgical training systems, tools, apparatuses, software, and methods for performing medical procedures in a simulated environment (e.g., cross reality, virtual reality, mixed reality, or augmented reality). In some embodiments, a system described herein provides graphic simulations of a medical surgery that deliver a user realistic feedback (e.g., haptic feedback) from a computer interface tool representing a virtual surgical instrument displayed in the simulation. In some embodiments, the training system provides consistent, realistic learning experiences for surgeons, trainees, new clinicians, or students.

In some embodiments, disclosed herein is a computer based surgical training system, comprising a processor, a hand-held component operatively coupled to the processor, and a non-transitory computer readable storage medium encoded with a computer program configured to communicate with the processor. In some embodiments, the system combines a sense of presence with a unique sense of touch to create a near-real operating experience, feel, and interaction with a patient. In some embodiments, a user of the system, e.g., a surgeon or trainee, can feel the interaction with tissue and real-time feedback. In some embodiments, the system disclosed herein provides a safe, measurable and repeatable involvement with medical training in procedures including orthopedic surgery, e.g., spinal pedicle screw, total knee arthroplasty, total hip arthroplasty (posterior, or anterior), laparoscopic surgery, general surgery, cardiovascular surgery, brain or neural surgery, and otolaryngology (ear, nose, throat) surgery.

The details of one or more inventive embodiments are set forth in the accompanying drawings, the claims, and the description herein. A feature, object, or advantage of an inventive embodiment disclosed and contemplated herein can be combined with that of any other embodiment disclosed and contemplated herein, unless explicitly excluded.

Virtual Simulated Items and Environment

Disclosed herein, in some aspects, is a haptic tool that is a simulated item that can affect or interact with a second simulated item (e.g., haptic target). A haptic target is a simulated item that can be affected by a haptic tool. In some embodiments, the haptic tool evokes a haptic response from the haptic target.

Disclosed herein, in some aspects, is a virtual surgical instrument. In some embodiments, the virtual surgical instrument is a haptic tool that affects a haptic feedback on a virtual object. In some embodiments, the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof. In some embodiments, the virtual surgical instrument elicits a haptic response from the haptic target.

Disclosed herein, in some aspects, is a virtual object that can be a haptic target that is affected by a virtual surgical instrument. In some embodiments, the virtual object comprises one or more anatomical features. In some embodiments, the virtual object comprises a representation of a tissue and/or organ. In some embodiments, the virtual object comprises a representation of one or more layers or sub-components or a tissue and/or organ. In some embodiments, the virtual object comprises a representation of at least one of a skin, cartilage, a bone, a muscle, an organ, blood, a blood vessel, tendon, and a nerve.

Disclosed herein, in some aspects, is a virtual surgical field that is a simulated environment surrounding a virtual object and/or a simulated environment within which one or more virtual objects are represented. In some embodiments, the virtual surgical field comprises an operating room or a part thereof, a screen displaying instruction or information, a diagnostic or planning image (e.g., x-ray image), a surgical tool, a microscope, a laser range finder, a camera, a surgical light, an endoscope, an ultrasound probe, a radiotherapy device, an interventional medical tool, a rehabilitative system for physical therapy, or any combination thereof. In some embodiments, the virtual surgical field comprises one or more representations of medical personnel such as a surgeon, nurse, or assistant. In some embodiments, all of the textures used within the virtual surgical field are referenced on a texture atlas. In some embodiments, each texture is associated with a set of unique UV coordinates. In some embodiments, one or more virtual objects within the virtual or simulated environment comprise a plurality of textures that are referenced in a texture atlas. In some embodiments, the virtual surgical field comprises one or more displays that show the positions of surgical tools with respect to pre- or intraoperative images. As a non-limiting example, in the case of a simulated virtual surgery of the spine, the virtual surgical field provides a display that shows 3D computed tomography of the spine before surgery has commenced (pre-operative image). This information helps the user plan and/or visualize the surgical operations to be performed. Next, while the surgery is ongoing, additional 3D computed tomography images are displayed (intraoperative imaging). Thus, the user is able to view images of the bony and soft tissues of the spine and the positioning of their surgical tools with respect to those tissues. In this way, the systems and methods disclosed herein can more accurately simulate the operating room by displaying pre- or intraoperative images within the virtual environment. In some embodiments, the virtual surgical field or virtual environment comprises one or more displays showing one or more pre- or intraoperative images. In some embodiments, the images show the position (s) of one or more surgical tools. In some embodiments, the images show the tissues that are being operated on or will be operated on during the virtual simulation. In some embodiments, these images include intraoperative images, such as two-dimensional fluoroscopic images, and preoperative three dimensional images generated using, for example, magnetic resonance imaging (MRI), computed tomography (CT) and positron emission tomography (PET). In some embodiments, the systems and methods disclosed herein use a tracking or localizing system that locates markers attached or fixed to a physical object, such as an instrument (e.g., the hand-held component corresponding to a virtual surgical instrument), and track the position of markers. For example, this allows for movement of the hand-held component to be detected and then depicted or translated into the virtual environment. Alternatively or in combination, the hand-held component can be physically coupled or wired that allows its movement and/or an applied force (by a user) to be detected by one or more sensors and then depicted in the virtual environment. In some embodiments, these tracking systems are optical, magnetic, or acoustic systems. In some embodiments, optical systems have a stationary stereo camera pair that observes passive reflective markers or active infrared LEDs attached to the tracked tools. In some embodiments, magnetic systems have a stationary field generator that emits a magnetic field that is sensed by small coils integrated into the tracked tools. In some embodiments, the virtual surgical field comprises a display of one or more diagnostic or planning image(s), for example, x-ray images, computed tomography images, MRI images, MRA images, MR spectrometric images, PET images, MRV images, SPECT images, CEMRV images, CT angiographic images, CT myelographic images, MR myelographic images, flair images, two-dimensional fluoroscopic images, three-dimensional fluoroscopic images, two-dimensional ultrasonic images, three-dimensional ultrasonic images, ultrasound microscopy images, laparoscopic ultrasound images, optical images, isotopic images, laser depth maps, line arts, sketches, "cartoon" representations, holographic images, or any combination thereof.

Hand-Held Components

Disclosed herein, in some aspects, is a hand-held component. In some embodiments, the hand-held component is configured for manual manipulation. In some embodiments, the hand-held component is an electro-mechanical device that communicates with a user and is configured to be held by the user's hand(s). In some embodiments, the hand-held component provides haptic feedback based on one or more interactions in the simulated or virtual environment. In some embodiments, the hand-held component provides haptic feedback from interaction between a haptic tool and a haptic target. In some embodiments, a hand-held component allows a user to use a virtual surgical instrument to touch and manipulate virtual objects within the virtual surgical field. The hand-held component may be connected to a processor wirelessly or via a connector, e.g., a USB cable or coaxial cable or other cable. The processor may be a central processing unit ("CPU") located in a laptop computer or desktop computer, or other device whether hand-held or not, and which may display the virtual surgical field on a monitor screen or other display. In some embodiments, the hand-held component comprises an arm, a keyboard, a pointer, a wand, a joystick, a mouse, a roller, a grasper, a handle, or a glove. In some embodiments, the hand-held component comprises two arms configured to provide haptic feedback. In some embodiments, before use, the hand-held component is calibrated with a software/computer program disclosed herein.

In some embodiments, the hand-held component is attached or coupled to a base. In some embodiments, the hand-held component is configured to pivot, rotate, translate, and/or otherwise move in relation to the base to which it is attached. In some embodiments, the hand-held component is connected to a base by one or more wires or cables. In some embodiments, the hand-held component is connected to a base by a joint. In some embodiments, the base comprises the processor and/or is in communication with the processor. In some embodiments, the hand-held component comprises a power source or connection such as, for example, a power cable or a battery (single-use or rechargeable). In some embodiments, the hand-held component comprises one or more motors that provide haptic feedback such as, for example, pressure, resistance, vibrations, and other tactile feedback. In some embodiments, the hand-held component is attached to a base and provides one or more degrees of freedom. In some embodiments, the hand-held component provides at least two, at least three, at least four, at least five, at least six, or at least seven degrees of freedom. The hand-held component can provide freedom of motion such as, for example, moving up and down, moving left and right, moving forward and backward, swiveling left and right, tilting forward and backward, and pivoting side to side. In some embodiments, the hand-held device comprises a chain of one or more links connected by joints. In some embodiments, each joint provides one or more degrees of freedom (e.g., moving left and right or rotation). In some embodiments, the chain of links is attached or secured to a base.

In some embodiments, a haptic feedback felt by a user holding the hand-held components comprises pressure, force, velocity, motion, sensation, position, depth, width, surface, layer, contour, density, texture, resistance, direction, hardness, stiffness, softness, contraction, elasticity, flexibility, release, freedom, torque, rotation, contact, collision, any combination thereof, or any degree, magnitude, or duration thereof. In some embodiments, the force corresponds to a gripping of the object of interest with a virtual surgical instrument. In some embodiments, a degree of haptic feedback is determined as a degree of sensation, a degree of rotation, degree of retraction, degree of firmness, degree of freedom (DOF), magnitude, duration of a signal/feedback, or dynamic property of the force and/or torque, or any combination thereof. The haptic interaction forces and/or torques may be repulsive, attractive, frictional, viscous, impulsive, detent, regulatory (for example designed to maintain cutting speeds or feed rates), or any combination thereof. In some embodiments, a haptic feedback comprises a variation of signal in terms of types and degrees/intensities over a duration, for example, feeling a change from a firm density to a softer texture for a certain period of duration, when scorching cartilage white whilst slowly penetrating with an electrocautery or cauterizing pen.

In some embodiments, a type or degree of haptic feedback is connected to a user's particular virtual experience. For example, when a user is cutting through a dense tissue such as bone, the hand-held component generates a resistive force on a hand of the user. In some embodiments, the amount of resistance generated is directly related to the virtual tissue type. Another example, when a user is using a virtual surgical instrument such as a sharp scalpel, the hand-held component generates a realistically varying degree of resistance and difficulty such that the sharp scalpel cleanly cuts skin and muscle, barely marks cortical bone, and cuts cartilage with resistance and difficulty. Another example, when a user is using a virtual surgical instrument such as a sagittal saw, the hand-held component generates a motion that the sagittal saw oscillates and tears skin, a pressure or contact for a certain period of duration from cleanly cutting bone, and a torque and strength of force from cutting cartilage with ripping action.

Users' Experience

A user disclosed herein is a human subject e.g., a surgeon, a trainee, a clinician, or a student who uses a system, device, object, instrument, software, or method disclosed herein. In some embodiments, the user holds a hand-held component, which interacts with a processor, to control a virtual surgical instrument to perform a realistically simulated surgery. In some embodiments, the processor presents a virtual image on a display and allows the user to touch, manipulate, modify, or otherwise interact with virtual objects within a virtual surgical field. In some embodiments, the display is configured to show movement of the virtual surgical instrument based on motions of the hand-held component and to provide feedback (e.g., haptic feedback) to the user holding the hand-held component depending on the position of the virtual surgical instrument. In some embodiments, the display is head mounted such that the virtual image may be presented on a display screen located on a virtual reality headset, helmet, googles, goggles, eyeglasses, or other headgear. In some embodiments, the system, methods, and software disclosed herein allow the user to perform simulated surgery while in a complete virtual world (e.g., as viewed through the display).

In some embodiments, a user's experience comprises receiving an input generated by a hand-held controller, determining a location in space of a virtual surgical tool based on the input, and/or determining whether the virtual surgical tool contacts an object associated with a haptic inside the virtual surgical environment, and if it does, next determining at least one vertex associated with the contact, retrieving haptic information from at least one UV coordinate associated with the vertex, and/or transmitting the haptic through the controller.

FIG. 1 illustrates an example how a user (101) engages a system disclosed herein with a virtual reality (VR) headset (102), a base comprising a processor (103) operatively coupled to a hand-held component (104)—two haptic arms that control a virtual object and receives feedback, and a computer (105) comprising a computer program configured to communicate with the processor.

In some embodiments, a virtual surgical field disclosed herein represents one of many surgical fields available from the system, and each surgical field provides a different experience for a user, e.g., a hip replacement surgery, a knee replacement surgery, and a spinal surgery.

Figure 2:
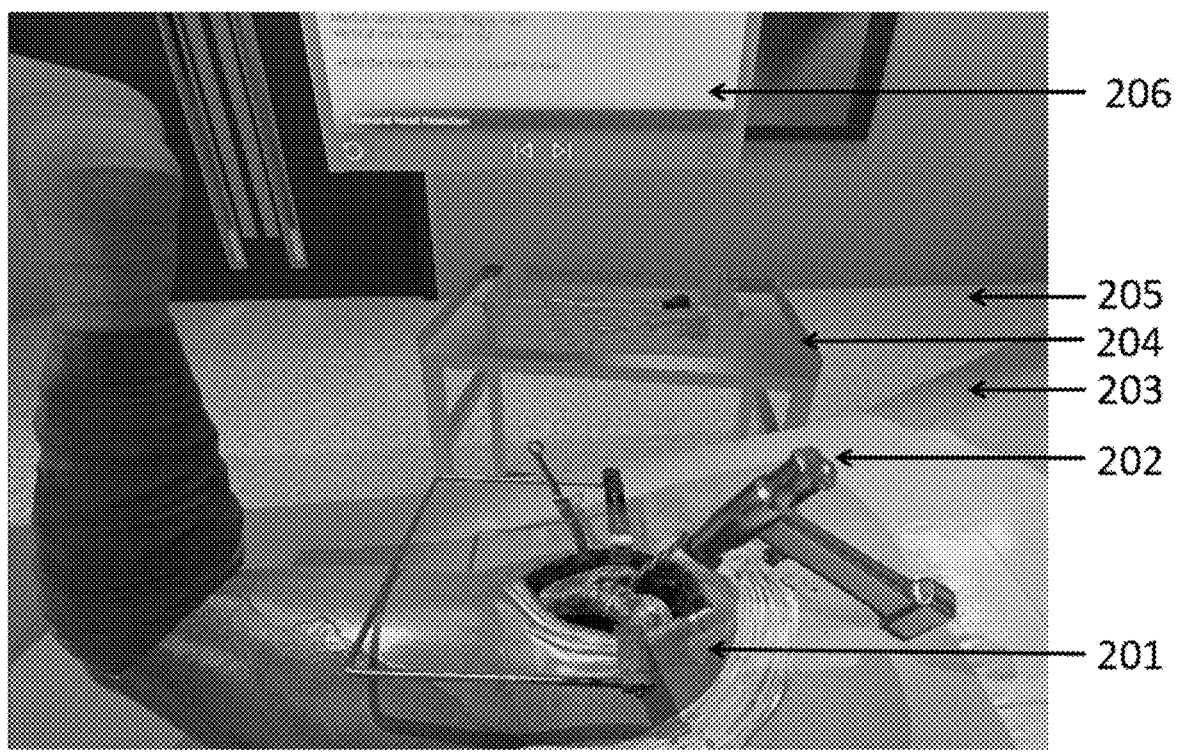
FIG. 2 shows an example of a virtual operation room for a hip replacement surgery.

FIG. 2 shows an exemplary virtual operation room for a hip replacement surgery. This figures shows part of what a user engaged with the system actually sees, including a virtual object-hip (201), virtual surgical instruments such as a hammer (202), and a virtual surgical field including an operating table (203), a surgical instrument cart (204) with various tools, a floor (205), and a screen (206) from which the user receives instruction to conduct the surgery.

Figure 3:
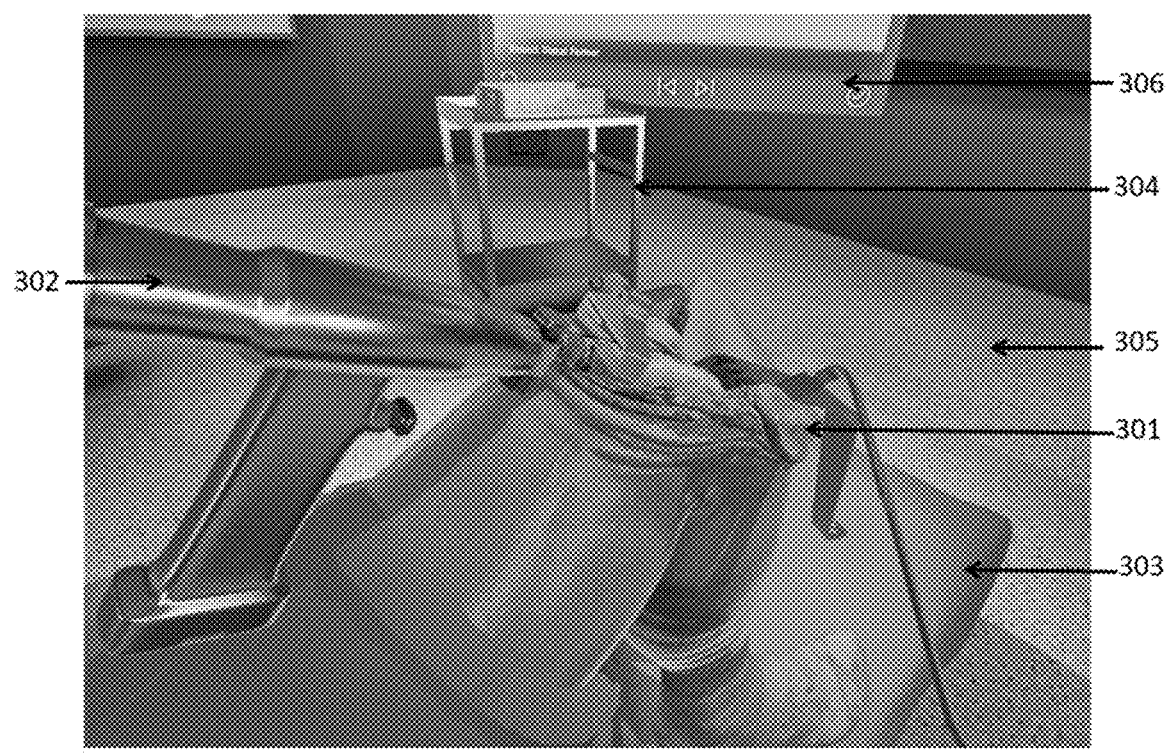
FIG. 3 shows an example of a virtual operation room for a knee replacement surgery.

FIG. 3 shows an exemplary virtual operation room for a knee replacement surgery. This figures shows part of what a user engaged with the system actually sees, including a virtual object-knee (301), virtual surgical instruments such as a power drill (302), and a virtual surgical field including an operating table (303), a surgical instrument cart (304) with various tools, a floor (305), and a screen (306) from which the user receives instruction to conduct the surgery.

Figure 4:
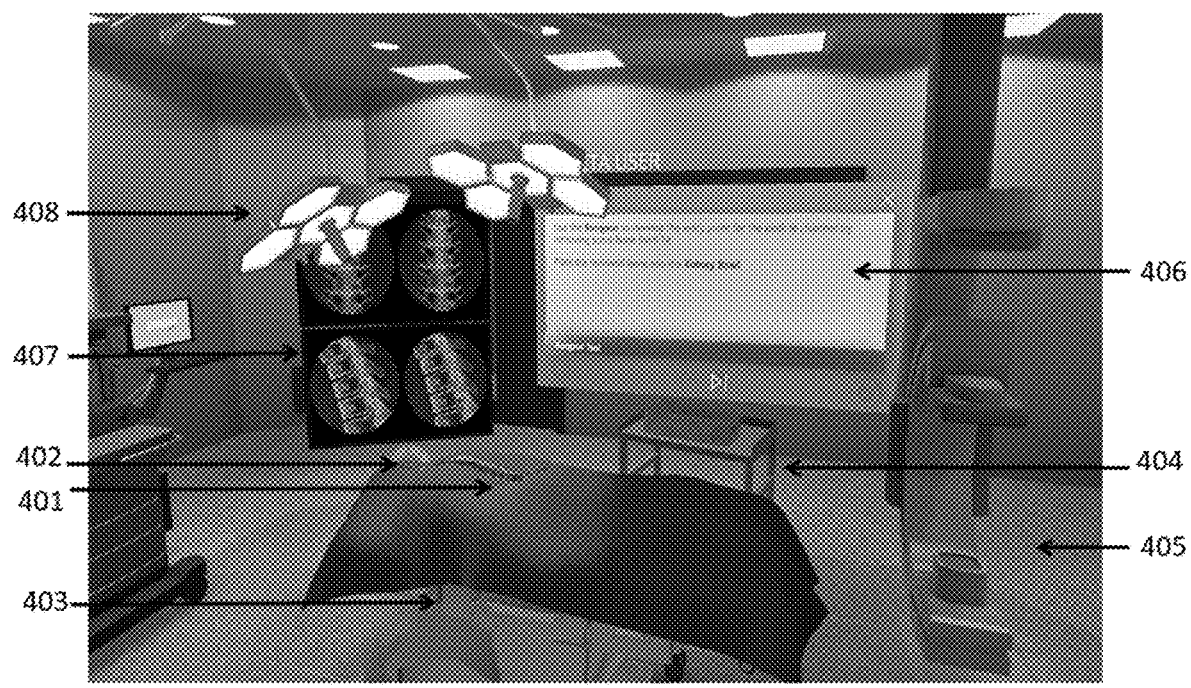
FIG. 4 shows an example of a virtual operation room for a spinal surgery.

FIG. 4 shows an exemplary virtual operation room for a spinal surgery. This figures shows part of what a user engaged with the system actually sees, including a virtual object-spine (401), virtual surgical instruments such as a retractor (402), a virtual surgical field including an operating table (403), a surgical instrument cart (404) with various tools, a floor (405), a screen (406) from which the user receives instruction to carry out the surgery, x-ray images (407), and surgical lights (408).

Figure 5:
FIG. 5 is a close-up image of the virtual environment shown in FIG. 4.

FIG. 5 is a close-up image of the exemplary virtual environment shown in FIG. 4, in which a user actually sees the virtual object-spine (501), virtual surgical instruments such as the retractor (502) and a periosteal elevator (503), the surgical instrument cart (504), the floor (505), the screen (506), the x-ray image (507), and a surgical basin container (508).

In some embodiments, a system disclosed herein is capable of providing a user an individual virtual access to a three-dimensional ("3D") environment. Such system may serve as surgical educational or training tools providing a user the ability to practice procedures within a virtual environment using a virtual surgical instrument. In some embodiments, the system can provide a realistic and efficient method to obtain, practice, and refine surgical skills with concomitant instructional feedback and evaluation. In some embodiments, the system allows the user to practice various surgical procedures including creating lines of incision and creating osteotomies in either a 2D or 3D environment. In some embodiments, the system allows the user to "feel" the various densities of bone when preparing osteotomies and to angle the virtual surgical instrument appropriately. For example, the system provides haptic feedback to the user that a virtual surgical instrument such as an electrocautery/ cauterizing pen deforms and burns skin brown, scorches bone white without penetrating, and scorches cartilage white whilst slowly penetrating.

In some embodiments, a system disclosed herein is customized to use actual digital imaging data from an actual patient and allow a user to practice an upcoming or proposed surgery prior to the real operation. For example, digital imaging data of a patient can be produced by taking at least one X-ray or CAT scan image of the area where the surgery is to be performed and then shown in the virtual or simulated environment. Alternatively or additionally, other imaging data may be used such as from an MRI or scanned image of a surface model of the surgical site. This data is can be used to virtually reconstruct the patient's actual surgical field to be used in the virtual simulation. Such data may include a specific patient's bone structure and formation or bone tissue. In another example, this data may be useful for creating a prosthesis for the patient after the surgery has concluded. The actual digital imaging data may be stored within a database. The database can be a local database (e.g., stored on a local server) or a remote network or cloud database. In some embodiments, the database includes data relating to nonphysical properties or other medical information of a specific patient, such as a patient's medical history, known allergies, and illnesses. In some embodiments, the database may include information pertaining to a patient's treatment plan or procedure. In some embodiments, a processor herein may access the data contained within the database and provide the user access to this data. In some embodiments, a user may access and upload a patient's digital data to the system and use the data to practice a specific patient's planned surgery within a virtual environment.

Systems for Determining Haptic Feedback

In some embodiments, a system as described herein is configured to determine a type and degree of haptic feedback that a user experiences. In some embodiments, a system as described herein comprises a sensor, e.g., a hand-held component, for receiving haptic feedback. In some embodiments, the haptic feedback is associated with a texture. In some embodiments, the haptic feedback comprises a sensation that represents the response of a texture to a force.

In some embodiments, a system as described herein comprises a network element for communicating with a server. In some embodiments, the server is part of the system. In some embodiments, the system is configured to upload to and/or download data from the server. In some embodiments, the server is configured to store sensor data, haptic feedback type(s) and degree(s), and/or other information for the subject. In some embodiments, the server is configured to store historical data for the subject. In some embodiments, the server is configured to backup data from the system or apparatus. In some embodiments, a system as described herein is configured to perform any of the methods described herein.

In some embodiments, a system as described herein comprises a processor; a hand-held component operatively coupled to the processor; and a non-transitory computer readable storage medium encoded with a computer program configured to communicate with the processor. In some embodiments, a processor disclosed herein is part of or linked to a computer and includes or is operatively coupled to a graphics card, a monitor, and/or a virtual reality headset. In some embodiments, the computer program causes the processor to: (i) locate a texture from a plurality of textures positioned on a texture atlas, wherein the texture is located using an offset value that is based on at least one UV coordinate; (ii) map the texture of interest onto the at least one virtual object; (iii) display the at least one virtual object as part of a virtual surgical field; (iv) receive an input from the hand-held component when a user moves the hand-held component; and (v) display an interaction in the virtual surgical field between a virtual surgical instrument and the object of interest based on the input. In some embodiments, the computer program further causes the processor to display a movement of the virtual surgical instrument in the surgical field in the same direction as a movement of the hand-held component based on the input. In some embodiments, the interaction comprises moving the object of interest with the virtual surgical instrument and the computer program further causes the processor to display a seamless movement of the texture along with the movement of the object of interest. In some embodiments, the interaction comprises cutting the object of interest and the computer program further causes the processor to display an interior texture of the virtual object that is different than the texture, and wherein the interior texture is positioned on the texture atlas and has a unique set of UV coordinates. In some embodiments, the computer program further causes the processor to simultaneously display the texture and the inner texture and wherein the processor draws upon the texture atlas once. In some embodiments, the interaction comprises applying a force to the object of interest with the virtual surgical instrument and the computer program further causes the processor to display a response of the texture to the force. In some embodiments, the interaction is displayed seamlessly during the period that the interaction is displayed.

In some embodiments, the system or apparatus is configured to encrypt data. In some embodiments, data on the server is encrypted. In some embodiments, the system or apparatus comprises a data storage unit or memory for storing data. In some embodiments, data encryption is carried out using Advanced Encryption Standard (AES). In some embodiments, data encryption is carried out using 128-bit, 192-bit, or 256-bit AES encryption. In some embodiments, data encryption comprises full-disk encryption of the data storage unit (e.g., encrypting the entire hard drive on a server or apparatus). In some embodiments, data encryption comprises virtual disk encryption (e.g., encrypting a folder containing sensor data files for a subject). In some embodiments, data encryption comprises file encryption (e.g., encrypting sensor data files for a subject). In some embodiments, data that is transmitted or otherwise communicated between the system or apparatus and other devices or servers is encrypted during transit. In some embodiments, wireless communications between the system or apparatus and other devices or servers is encrypted. As an example, an apparatus that is integrated with a haptic tool sends and/or receives data wirelessly using an encrypted data channel. In some embodiments, data in transit is encrypted using a Secure Sockets Layer (SSL). In some embodiments, access to data stored on the system or apparatus as described herein requires user authentication. In some embodiments, access to data stored on the server as described herein requires user authentication.

An apparatus as described herein comprises a digital processing device that includes one or more hardware central processing units (CPUs) or general purpose graphics processing units (GPGPUs) that carry out the device's functions. The digital processing device further comprises an operating system configured to perform executable instructions. The digital processing device is optionally connected to a computer network. The digital processing device is optionally connected to the Internet such that it accesses the World Wide Web. The digital processing device is optionally connected to a cloud computing infrastructure. Suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein.

Typically, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

A digital processing device as described herein either includes or is operatively coupled to a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

A system or method as described herein can be used to generate, determine, and/or deliver a degree of haptic feedback which may then be used to determine whether a subject value falls within or outside of a threshold value. In addition, in some embodiments, a system or method as described herein generates a database as containing or comprising one or more haptic feedback degrees. In some embodiments, a database herein provides a relative risk of presence/absence of a status (outcome) associated with haptic feedback that fall either within or outside of a threshold value.

Some embodiments of the systems described herein are computer based systems. These embodiments include a CPU including a processor and memory which may be in the form of a non-transitory computer-readable storage medium. These system embodiments further include software that is typically stored in memory (such as in the form of a non-transitory computer-readable storage medium) where the software is configured to cause the processor to carry out a function. Software embodiments incorporated into the systems described herein contain one or more modules.

In various embodiments, an apparatus comprises a computing device or component such as a digital processing device. In some of the embodiments described herein, a digital processing device includes a display to send visual information to a user. Non-limiting examples of displays suitable for use with the systems and methods described herein include a liquid crystal display (LCD), a thin film transistor liquid crystal display (TFT-LCD), an organic light emitting diode (OLED) display, an OLED display, an active-matrix OLED (AMOLED) display, or a plasma display.

A digital processing device, in some of the embodiments described herein includes an input device to receive information from a user. Non-limiting examples of input devices suitable for use with the systems and methods described herein include a keyboard, a mouse, trackball, track pad, or stylus. In some embodiments, the input device is a touch screen or a multi-touch screen.

The systems and methods described herein typically include one or more non-transitory computer-readable storage media encoded with a program including instructions executable by the operating system of an optionally networked digital processing device. In some embodiments of the systems and methods described herein, the non-transitory storage medium is a component of a digital processing device that is a component of a system or is utilized in a method. In still further embodiments, a computer-readable storage medium is optionally removable from a digital processing device. In some embodiments, a computer-readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Typically the systems and methods described herein include at least one computer program, or use of the same. A computer program includes a sequence of instructions, executable in the digital processing device's CPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages. The functionality of the computer-readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Typically, the systems and methods described herein include and/or utilize one or more databases. In view of the disclosure provided herein, those of skill in the art will recognize that many databases are suitable for storage and retrieval of baseline datasets, files, file systems, objects, systems of objects, as well as data structures and other types of information described herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Figure 6:
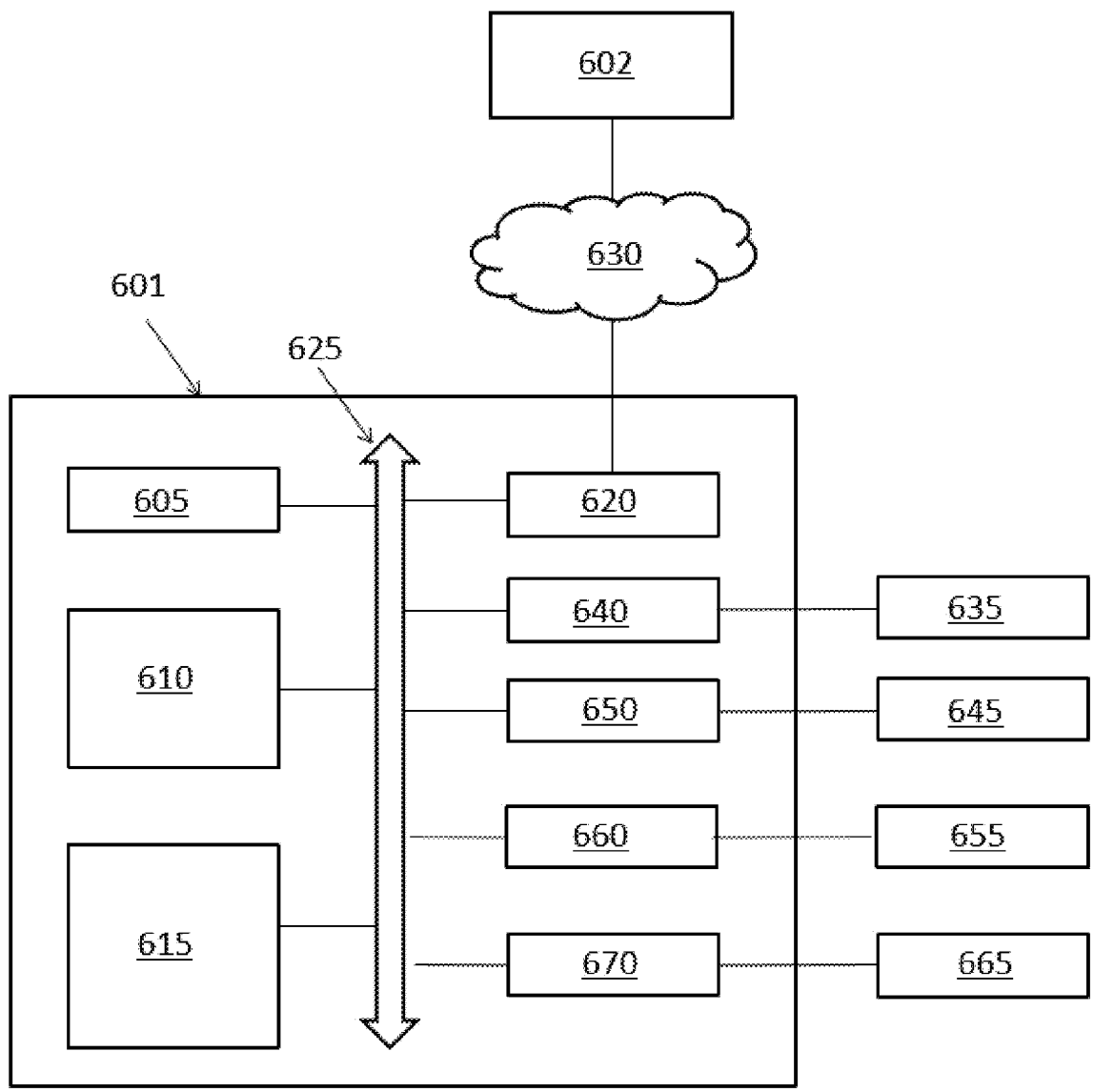
FIG. 6 shows an embodiment of a computer system as described herein.

FIG. 6 shows exemplary embodiments of a system as described herein comprising an apparatus such as a digital processing device 601. The digital processing device 601 includes a software application configured to determine visual feedback and/or a type and degree of haptic feedback to a user. The digital processing device 601 may include a central processing unit (CPU, also "processor" and "computer processor" herein) 605, which can be a single core or multi-core processor, or a plurality of processors for parallel processing. The digital processing device 601 also includes either memory or a memory location 610 (e.g., random-access memory, read-only memory, flash memory), electronic storage unit 615 (e.g., hard disk), communication interface 620 (e.g., network adapter, network interface) for communicating with one or more other systems, and peripheral devices, such as cache. The peripheral devices can include storage device(s) or storage medium 665 which communicate with the rest of the device via a storage interface 670. The memory 610, storage unit 615, interface 620 and peripheral devices are configured to communicate with the CPU 605 through a communication bus 625, such as a motherboard. The digital processing device 601 can be operatively coupled to a computer network ("network") 630 with the aid of the communication interface 620. The network 630 can comprise the Internet. The network 630 can be a telecommunication and/or data network.

The digital processing device 601 includes input device(s) 645 to receive information from a user, the input device(s) in communication with other elements of the device via an input interface 650. The digital processing device 601 can include output device(s) 655 that communicates to other elements of the device via an output interface 660.

The CPU 605 is configured to execute machine-readable instructions embodied in a software application or module. The instructions may be stored in a memory location, such as the memory 610. The memory 610 may include various components (e.g., machine readable media) including, but not limited to, a random access memory component (e.g., RAM) (e.g., a static RAM "SRAM", a dynamic RAM "DRAM, etc.), or a read-only component (e.g., ROM). The memory 610 can also include a basic input/output system (BIOS), including basic routines that help to transfer information between elements within the digital processing device, such as during device start-up, may be stored in the memory 610.

The storage unit 615 can be configured to store files, such as health or risk parameter data, e.g., individual health or risk parameter values, health or risk parameter value maps, and value groups. The storage unit 615 can also be used to store operating system, application programs, and the like. Optionally, storage unit 615 may be removably interfaced with the digital processing device (e.g., via an external port connector (not shown)) and/or via a storage unit interface. Software may reside, completely or partially, within a computer-readable storage medium within or outside of the storage unit 615. In another example, software may reside, completely or partially, within processor(s) 605.

Information and data can be displayed to a user through a display 635. The display is connected to the bus 625 via an interface 640, and transport of data between the display other elements of the device 601 can be controlled via the interface 640.

Methods as described herein can be implemented by way of machine (e.g., computer processor) executable code stored on an electronic storage location of the digital processing device 601, such as, for example, on the memory 610 or electronic storage unit 615. The machine executable or machine readable code can be provided in the form of a software application or software module. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

In some embodiments, a remote device 602 is configured to communicate with the digital processing device 601, and may comprise any mobile computing device, non-limiting examples of which include a tablet computer, laptop computer, smartphone, or smartwatch. For example, in some embodiments, the remote device 602 is a smartphone of the user that is configured to receive information from the digital processing device 601 of the apparatus or system described herein in which the information can include a summary, sensor data, types and degrees of haptic feedback, or other data. In some embodiments, the remote device 602 is a server on the network configured to send and/or receive data from the apparatus or system described herein.

Some embodiments of the systems and methods described herein are configured to generate a database comprising one or more types and degrees of haptic feedback and/or threshold value. A database, as described herein, is configured to function as a user's learning tool or a lookup table to evaluate a user's performance, e.g., after a simulated surgery is completed. In some embodiments, types and degrees of haptic feedback are presented in a database so that a user is able to identify whether a parameter of a specific subject falls within or outside of a threshold value. In some embodiments, the database is stored on a server on the network, or stored locally with data backup provided by a server. In some embodiments the database is stored locally on the apparatus or the system.

Figure 12:
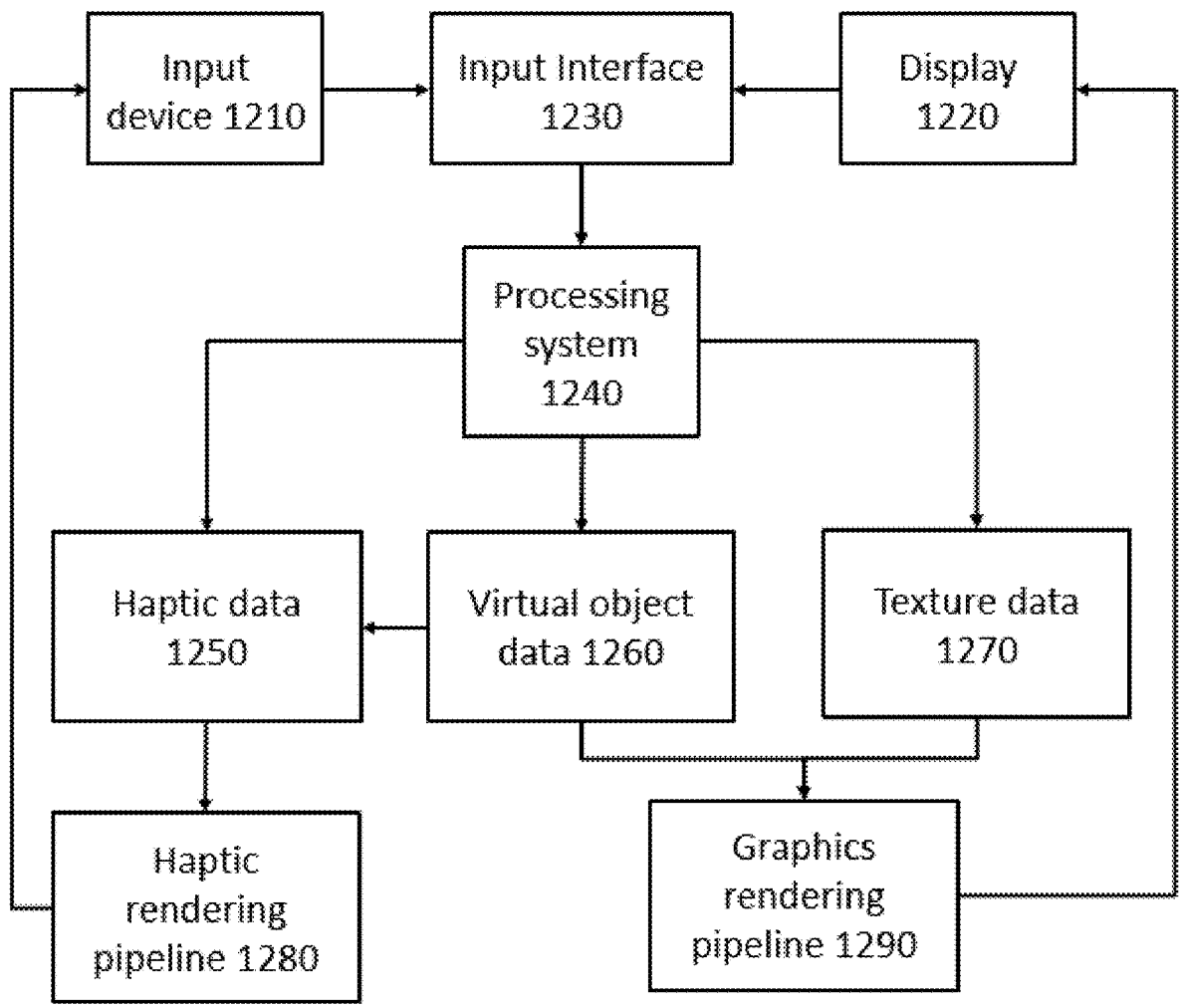
FIG. 12 shows an embodiment of a haptic and graphics rendering system for carrying out any of the haptic feedback and/or visual feedback or rendering functions described herein.

FIG. 12 shows an embodiment of a haptic and graphics rendering system for carrying out any of the haptic feedback and/or visual feedback or rendering functions described herein. An input device 1210 that is manipulated by a user and a display 1220 can provide input information to the processing system 1240 through the input interface 1230. An input device 1210 can be any number of devices such as, for example, a hand-held component that corresponds to a simulated surgical tool. The display 1220 provides visual information to the user and can include various computer displays or monitors including virtual reality headsets, projections, or other digital displays. The input information can include the position, orientation, or movement of the input device (e.g., motion tracking), and/or force of the movement or force exerted on the input device 1210 by a user. The input information can include the position, orientation, or movement of the display 1220 (e.g., motion tracking) such as, for example, a viewing angle of what the user is looking at in a virtual reality headset.

The processing system 1240 may access haptic data 1250 corresponding to the input device 1210 and/or a virtual object that the input device 1210 is interacting with within the virtual simulation in order to calculate a haptic feedback (e.g., standard haptic feedback data or alternatively bump map data as described herein) through the haptic rendering pipeline 1280. The haptic rendering pipeline 1280 then provides the signals to the input device 1210 to generate the determined haptic feedback. The haptic feedback may be a change in resistance to movement, a vibration or other tactile feedback. In the case of using bump mapping for haptic feedback, the complex or jagged surface on a 3D object represented by the bump mapping data may be used to determine a corresponding haptic feedback based on the "surface" that is being interacted with by the virtual tool. For example, the input information for the input device 1210 may be used in combination with the bump mapping data to determine the type and/or intensity of the feedback instead of using the 3D mesh of the virtual object. This approach modifies a technique used in the visual render pipeline and repurposes it for the haptic render pipeline.

The processing system 1240 may access virtual object data 1260 (e.g., polygonal voxel and/or mesh information) and texture data 1270 (e.g., a plurality of textures in a texture atlas) in order to render the virtual object with the appropriate textures mapped onto the voxels through the visual or graphics rendering pipeline 1290. The graphics rendering pipeline 1290 then provides the signals the display 1220 to show the visual information (e.g., the fully textured virtual object within the virtual simulation).

Texture Mapping

Disclosed herein, in some aspects, are systems and methods utilizing a texture mapping process to project textures onto three-dimensional objects for use in a virtual reality simulation such as in a cross reality, mixed reality, or augmented reality environment. In some embodiments, tri-planar mapping is used to apply textures to virtual objects. Traditional 3D computer graphics utilize tri-planar visual texture mapping. 3D meshes are created by various adaptive mesh algorithms (marching cubes/tetrahedrons etc.), which can create a surface by applying a texture using coordinates projected along three axes and blending them according to the vertex normals. Tri-planar mapping does not require UV coordinates that are stored per-vertex in a mesh. In some embodiments, UV mapping is used to apply textures to virtual objects. In some embodiments, UV mapping generally includes unwrapping a 3D mesh onto a two-dimensional plane, creating a texture, and projecting the texture onto the unwrapped 3D mesh. The 3D mesh can then be "wrapped up" with the finished texture on its three-dimensional mesh. Such UV mapping approaches require UV coordinates that are stored per-vertex in a mesh.

In some aspects, described herein are systems and methods for providing a virtual reality simulation such as, for example, a cross reality, mixed reality, or augmented reality simulation. In some embodiments, a tri-planar texture mapping process used to generate at least part of the virtual reality simulation (including mixed or augmented reality) such as three-dimensional objects that a user can interact with within the virtual environment inside the simulation. Tri-planar texture mapping is a process by which textures are applied to three-dimensional objects. In some instances, tri-planar texture mapping is used in the generation of virtual patients, or body parts or anatomic structures of a virtual patient in a medical simulation. Examples of medical simulations include surgery or surgical techniques. Medical simulations can be used to simulate surgery for training purposes.

In some embodiments, the simulation comprises one or more three-dimensional objects in the virtual reality environment (including mixed or augmented reality). In some embodiments, a 3D object comprises a 3D mesh having one or more textures. In some embodiments, each three-dimensional object has a texture. The texture may simulate one or more aspects of the object such as, for example, skin, connective tissue or fascia, blood vessels, nerves, or bone.

In some embodiments, the texture mapping process comprises obtaining a model of a three-dimensional object. The three-dimensional object may be modeled with a wire frame defining a plurality of polygonal surface areas. This wire frame provides the object with the three-dimensional shape, which may be a complex shape rather than a simple polyhedron. In some embodiments, the model is created as a polygon mesh using a 3D modeler. Accordingly, the object provides the shape that can be rendered using the appropriate textures.

In some embodiments, texture mapping is applied to one or more objects in the virtual simulation. The objects can include medical instruments or tools. Medical instruments or tools can include surgical instruments such as scalpels, forceps, retractors, clamps, specula, scopes, sealing devices such as surgical staplers, ultrasound tissue disruptors, and other instruments. In some instances, medical instruments include stethoscopes, catheters and guidewires, defibrillators, syringes, stents, suction devices, and other medical devices. Medical instruments or tools can often have a simpler shape or an assembly of simple shapes. Accordingly, in some embodiments, texture mapping is used to project textures onto medical instruments or tools using simpler mapping shapes such as, for example, cylindrical mapping in the case of a catheter. In some embodiments, the objects include simulated patients such as, for example, a virtual cadaver or an anatomic portion thereof. In some embodiments, the anatomic portion comprises an arm, a leg, a torso, a head and/or neck, or other body part. In some embodiments, the anatomic portion comprises textures and/or material types corresponding to the surface of a body part. In some embodiments, the textures or materials are mapped using tri-planar mapping. In some embodiments, the textures or materials include skin, hair, blood vessels (veins, arteries, capillaries, etc.), fascia, connective tissue, muscle, cartilage, bone, blood, and membranes such as the pleura, peritoneum, mediastinum, and pericardium.

Application of Texture Atlasing to Tri-Planar Mapping

In some aspects, the systems and methods for providing a virtual reality simulation (including cross reality, mixed reality, or augmented reality) utilize a texture atlas to provide a virtual object having multiple textures or materials. In some embodiments, the virtual reality simulation comprises one or more virtual objects having one or more material types. The virtual object may have at least two, three, four, five, six, seven, eight, nine, or ten or more material types. For example, in the case of a surgical simulation for training purposes, a virtual object may need to be rendered with multiple material types to provide a more accurate representation such as, for example, in the case of an arm that may have materials including an epidermis, muscles, blood vessels, and bone. Accordingly, an accurate representation of these materials in the virtual object may require the mapping of distinct textures onto multiple surfaces that make up the layers or subcomponents of the virtual object.

Tri-planar visual texture mapping is one approach for texturing the meshes created by various adaptive mesh algorithms (marching cubes/tetrahedrons etc.). It creates a near seamless surface by applying a texture using coordinates projected along three axes and blending them according to the vertex normals.

Figure 7A:
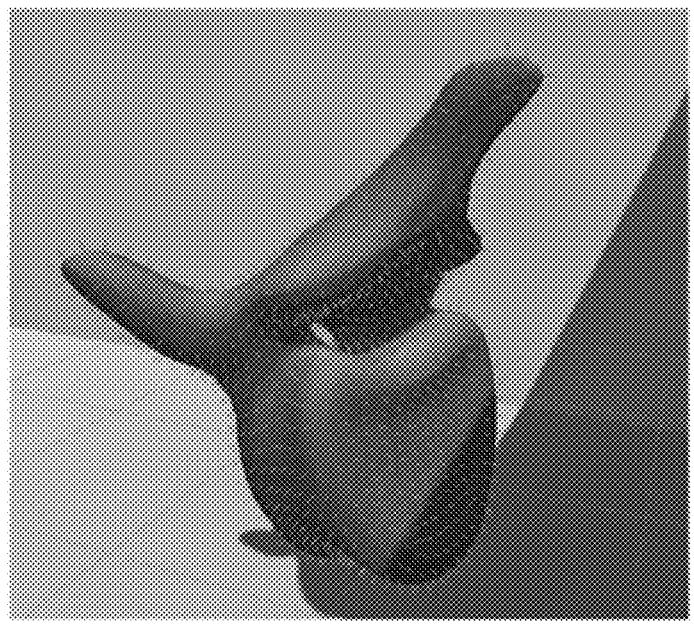
FIG. 7A and FIG. 7B show examples of traditional 3D computer simulated graphics.
Figure 7B:
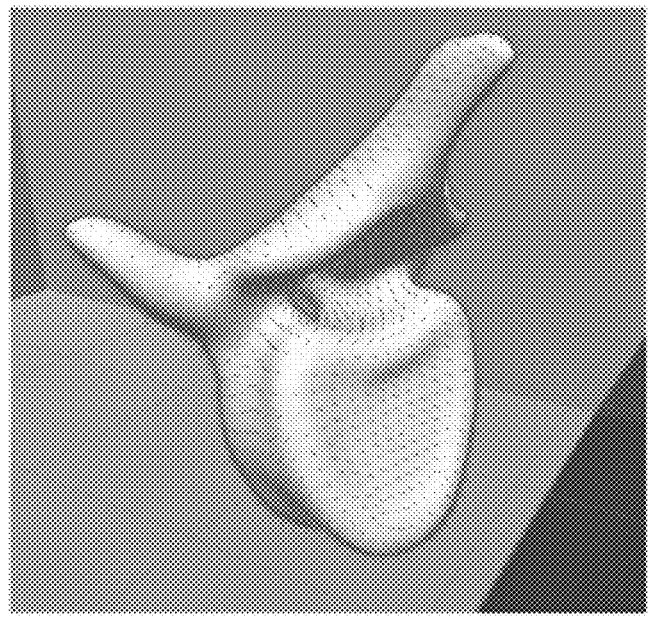

FIG. 7A and FIG. 7B show exemplary traditional 3D computer simulated graphics. FIG. 7A illustrates a computer simulated object having faces colored to show normal based blending. FIG. 7B illustrates computer simulated object having faces textured with single bone texture.

However, with such conventional methods, representation of multiple material types with respect to, for example, appearance (e.g. texture) and feel (e.g. haptic feedback) are not well supported and can leave a less than ideal visual representation and/or a downturn in rendering speed. With respect to virtual (or augmented or mixed) surgical experiences in particular, users are often rapidly penetrating virtual objects (e.g. bodies) and passing through different object layers (e.g. tissue layers) that respectively have different properties (e.g. texture and/or haptic properties). As a user penetrates a virtual object, each visual effect and/or haptic effect may need to be programmed and rendered into the space. This can result in a significant increase in code complexity and require the creation of multiple meshes which in turn require multiple draw calls to be made, increasing processor load on a traditional computer implemented system. For example, in the case of a surgical simulation, when the user penetrates the virtual object with a virtual scalpel, each visual effect corresponding to various parts or layers of the object needs to be programmed and rendered into the space.

Accordingly, in order to provide efficient processing of realistic visual and/or haptic data within a virtual (or augmented or mixed) reality surgical environment, in some embodiments, a system disclosed herein provides an improved approach that is to use the otherwise unused texture coordinates (also known as UV coordinates) to represent an offset into a texture atlas comprised of multiple surface textures to depict various materials, e.g., muscle, bone, cartilage, nerve fiber.

Figure 8A:
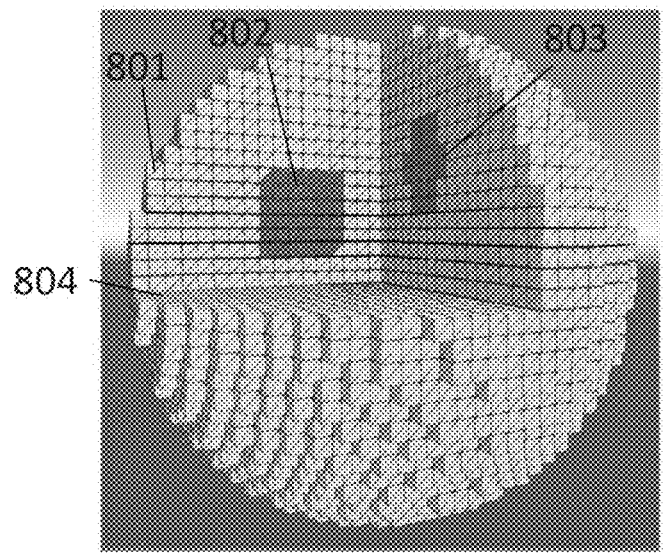
FIG. 8A shows a voxel data representation containing tissue type information indicated by the different colors.
Figure 8B:
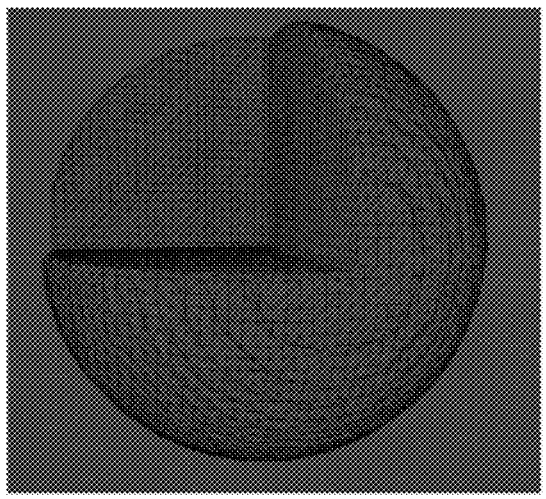
FIG. 8B shows a mesh generated from the same voxel data represented in FIG. 8A.
Figure 8C:
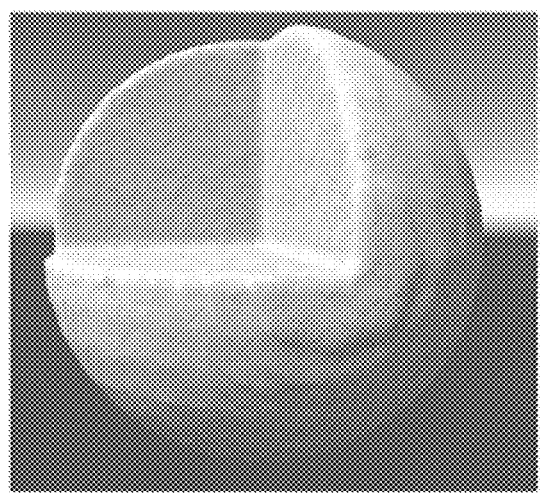
FIG. 8C shows a render of this mesh using a standard triplanar shader. The different tissue types may not be preserved.

FIG. 8A shows a voxel data representation containing tissue type information indicated by the different colors. As used herein, a voxel is well-known in the field as and represents a value on a grid in three-dimensional space. The individual voxels are shown as cubes that make up the roughly spherical three-dimensional object. An individual voxel 801 having no texture or a default texture is shown in FIG. 8A along with voxels having three distinct textures including, in this illustrative example, a red textured voxel 802, a blue textured voxel 803, and a green textured voxel 804. In some embodiments, a virtual object such as a tissue or organ is represented as voxel data that provides information regarding both its shape and texture(s). In some embodiments, the virtual object is composed of multiple materials, which may have corresponding textures. These materials may correspond to different textures in a texture atlas that is referenced by UV coordinates in the voxel data. FIG. 8B shows a mesh generated from the same voxel data represented in FIG. 8A. The three-dimensional mesh provides the shape of the three-dimensional object that is rendered in the visual render pipeline. In some embodiments, the voxel data is used to generate or render a three-dimensional mesh. FIG. 8C shows a render of this mesh using a standard triplanar shader. As shown, the different tissue types are not preserved in the mesh generated with the standard triplanar shader without reference to a texture atlas. Instead, the mesh in FIG. 8C has a single default texture, which may be inadequate for purposes of rendering complex objects made of multiple material types.

Figure 9A:
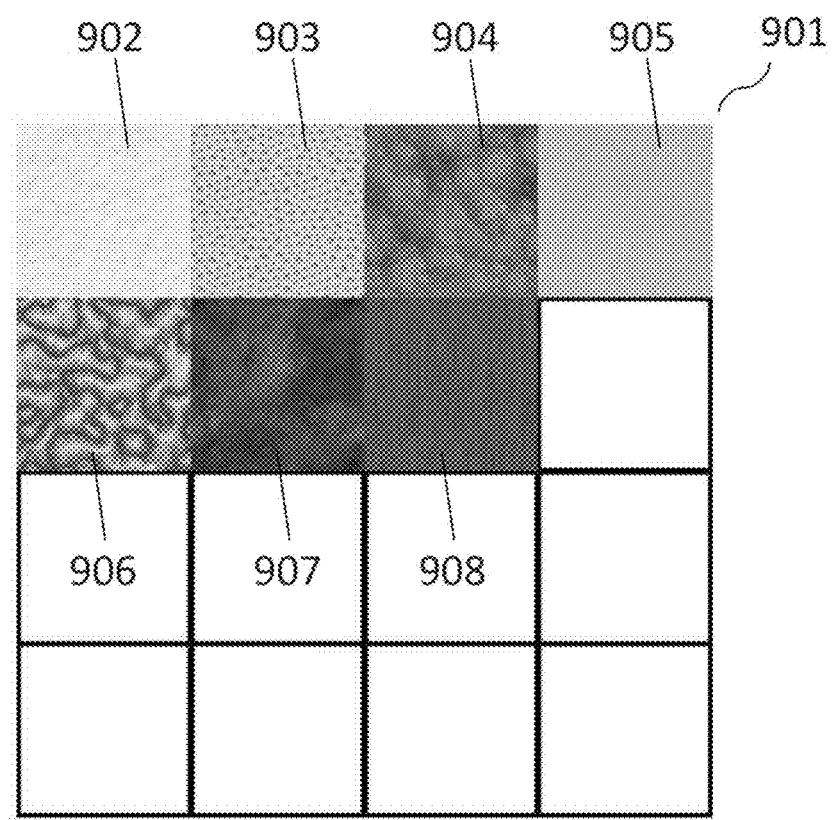
FIG. 9A shows the texture atlas where the textures for many tissue types have been combined.
Figure 9B:
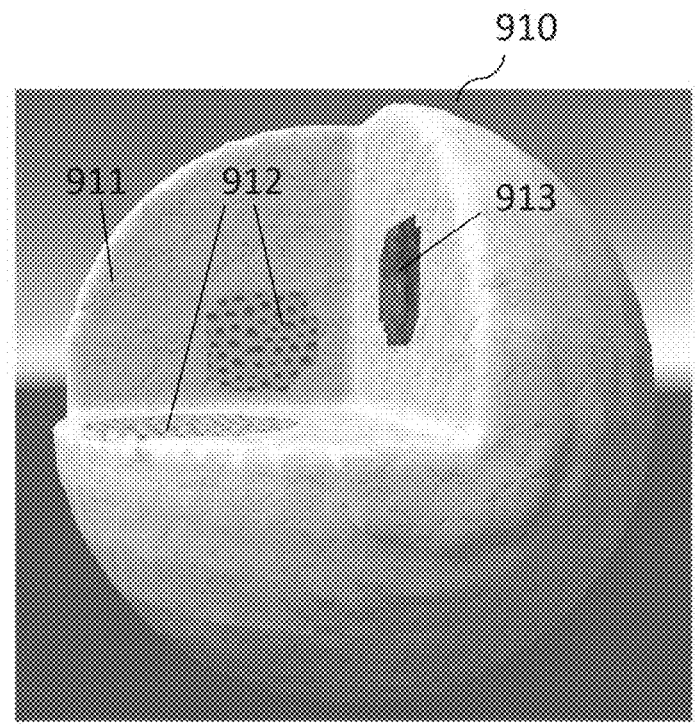
FIG. 9B shows a render of the mesh using a method, system, or software disclosed herein. The tissue type data in the voxel presentation from FIG. 8A were used to dynamically generate UV coordinates that can be stored in the mesh data. When these were used in conjunction with a texture atlas such as the one in FIG. 8A, the triplanar shader can visually represent the different tissue types that make up the model.

FIG. 9A shows a texture atlas 901 comprising the textures for many tissue types. In computer graphics, a texture atlas is an image containing a plurality of smaller images. In some embodiments, the texture atlas comprises smaller images of equivalent size. Alternatively, in some embodiments, the texture atlas comprises smaller images of more than one size. In some embodiments, each of the smaller images is drawn using a unique set of texture coordinates that allow it to be picked out of the texture atlas. Typically, for a given object, one draw call is needed for each material used on the object. Accordingly, the use of a texture atlas to store multiple textures as disclosed herein reduces the draw calls needed for that object. In some instances, batching is used when multiple objects are rendered. For example, draw calls for multiple objects can be batched if the objects share a material or texture atlas. Accordingly, the systems and methods disclosed herein provide important benefits to virtual simulations such as the reduction in draw calls needed for a given virtual object. In addition, in the case of a texture atlas storing textures for multiple objects, the systems and methods disclosed herein can allow draw calls for the various textures for the multiple objects to be batched. In FIG. 9B, a single object is shown, so the texture atlas of FIG. 9A can be used so batching is not required. Accordingly, in the case of dynamic or real-time rendering of visual information (e.g., in a real-time virtual simulation), storing multiple textures in a texture atlas allows for one or more objects having multiple textures to be rendered using fewer draw calls. Thus, the storage and/or treatment of the textures using the systems and methods disclosed herein is more resource efficient, especially in the scenario of virtual objects that need to be rendered to account for different material types as they are modified by user interaction in a virtual simulation. As an example, when a user is chipping away at the outer surface of the bone (cortical bone) to expose the interior bone (trabecular bone), the virtual object may need to be dynamically rendered in real-time to show both the deformity of the virtual bone and the texture of the increasingly exposed trabecular bone. Storage of the multiple textures in a single texture atlas reduces the computational steps required when making render-state changes. Accordingly, the texture atlas enhances efficiency by reducing the overhead of render-state changes.

Maintaining a high frame rate is essential for virtual reality simulations (including mixed or augmented reality) in order to reduce latency and perceivable lag. Draw calls are very computationally expensive, and the simulation of multiple objects with complex texture information can result in a large number of draw calls that generate lag and/or low frame rate. Reducing the number of draw calls is an important part of maintaining the high number of frames per second needed to provide effective virtual simulations. When rendering an object, a new draw call is required for each different material as it changes the render state, making an object containing multiple materials such as cortical bone, cancellous bone, and other materials very processor intensive, limiting the frame rate that can be achieved. By combining the different materials into one texture atlas, the number of draw calls needed to render an object is radically reduced, giving a performance boost that will improve the frame rate. Additionally, by using this texture atlas across multiple objects, the draw calls can be batched, leading to further performance improvements. Accordingly, the systems and methods disclosed herein provide virtual simulations that utilize a texture atlas comprising multiple textures that can be referenced using UV coordinates to render virtual objects using a reduced number of computational steps (e.g., draw calls).

In the illustrative example of the texture atlas 901 shown in FIG. 9A, the tissue types include cortical bone 902, trabecular bone 903, fat or adipose tissue 904, epidermis or skin 905, brain tissue 906, blood 907, and muscle tissue 908. The tissue types listed in FIG. 9A are merely exemplary embodiments, and other tissue types known in the medical field are contemplated for use according to the systems and methods disclosed herein. In this case, each of the material types in the texture atlas corresponds to a unique set of coordinates (e.g., UV coordinates). FIG. 9B shows a render of the mesh having multiple tissue types 910 using a method, system, or software disclosed herein. The tissue type data in the voxel presentation from FIG. 8A were used to dynamically generate UV coordinates that can be stored in the mesh data. In this case, the three-dimensional object or model has both XYZ coordinates that define the position of the vertices and UV coordinates that are used to reference or call the textures from the texture atlas. Accordingly, when these UV coordinates are used in conjunction with a texture atlas such as the one in FIG. 8A, a texture rendering process such as triplanar shading can visually represent the different tissue types that make up the model. As shown in FIG. 9B, the model or object 910 is rendered with textures corresponding to cortical bone 911, trabecular bone 912, and fat tissue 913. The systems and methods disclosed herein can utilize a texture atlas to represent any visually distinct tissue type.

Figure 10A:
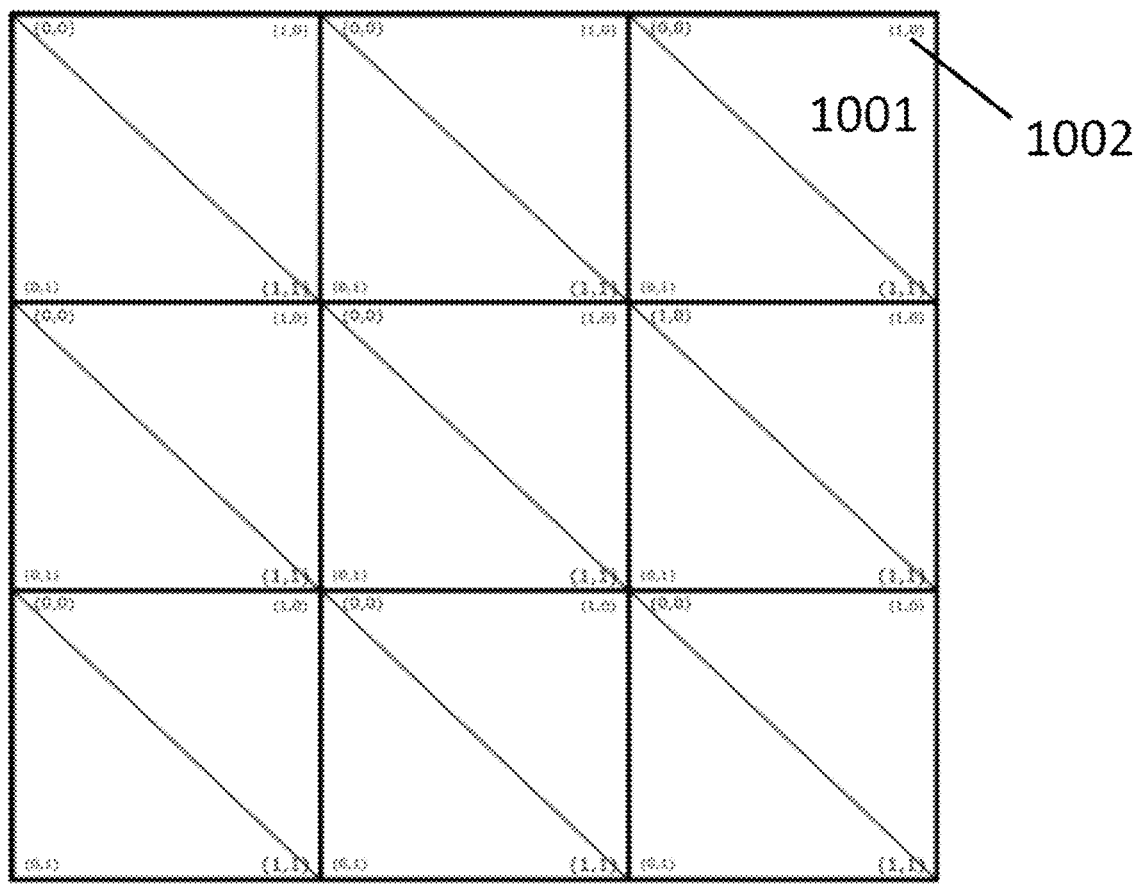
FIG. 10A shows an example of a UV coordinate structure.
Figure 10B:
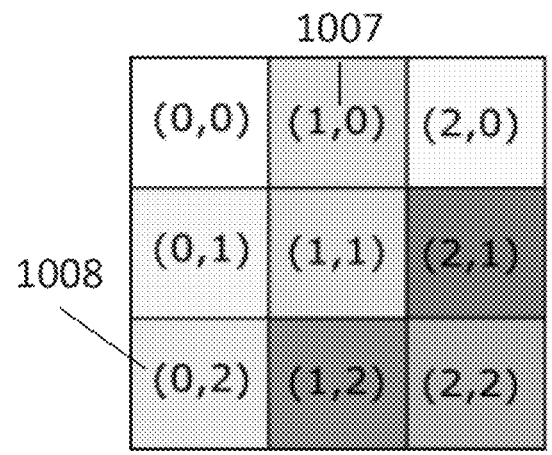
FIG. 10B shows an example of a texture atlas with corresponding UV coordinates.
Figure 10C:
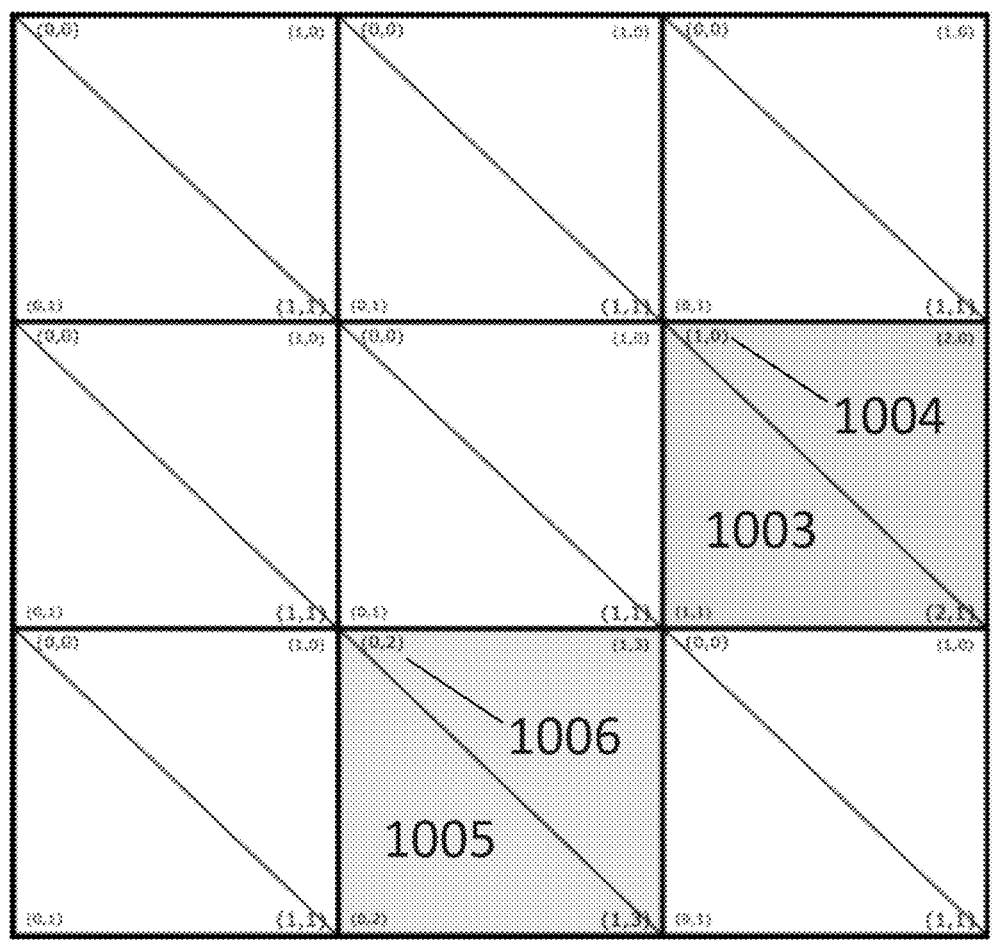
FIG. 10C shows a UV coordinate structure referencing a texture atlas in order to provide more textural details.

An example of the UV coordinates for a single texture or material is shown in FIG. 10A, and an example of a texture atlas is shown in FIG. 10B. In FIG. 10A, the nine squares correspond to nine quads with each quad defined by four UV coordinates. For example, one quad 1001 has four UV coordinates including (1, 0) 1002. The UV coordinate typically are based on two axis each having a range of [0, 1]. Thus, the top left UV coordinate for a quad is (0, 0), the top right UV coordinate is (1, 0), the bottom left UV coordinate is (0, 1), and the bottom right UV coordinate is (1, 1). In traditional UV mapping, a 2D image texture may be "wrapped" around the 3D mesh. However, disclosed herein are systems, methods, and software that generate modifiable virtual objects having complex texture information in real-time. In some embodiments, the systems and methods utilize UV coordinates that reference the texture atlas in order to provide a more efficient process for providing virtual objects with multiple surface textures. An example of a UV coordinate structure referencing a texture atlas in order to provide more textural details is shown in FIG. 10C. As shown, the UV coordinates in the top left corner of the middle right quad 1003 references "(1, 0)" 1004, which corresponds to the top middle green texture box 1007 in the texture atlas. The UV coordinates in the bottom middle quad 1005 references "(0, 2)" 1006, which corresponds to the bottom left cyan texture box 1008 in the texture atlas. Normally, these UV coordinates can only be used for static objects such as through UV unwrapping to texture a virtual object of a known shape beforehand, but the present systems, methods, and software utilize UV coordinates to reference a texture atlas to provide enhanced information on the textures or materials for dynamic representations such as voxels used in the virtual object or model. Thus, these UV coordinates are used in combination with the texture atlas to provide textures for the corresponding vertexes.

Figure 14:
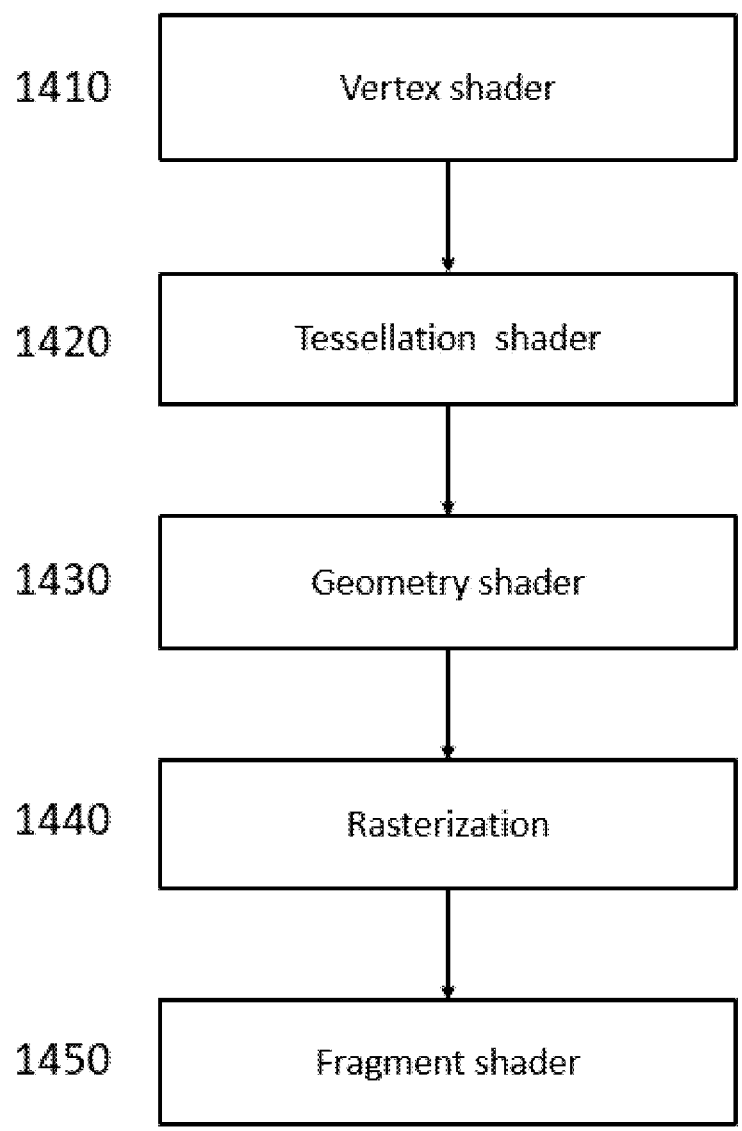
FIG. 14 shows an illustrative flow chart outlining processing steps or stages of a graphics rendering pipeline, for example, when using a texture atlas to render multiple textures on one or more meshes.

An non-limiting embodiment of a graphics rendering pipeline is shown in FIG. 14. The graphics rendering pipeline includes a sequence of processing steps or stages including a vertex shader 1410, tessellation shader 1420, a geometry shader 1430, rasterization 1440, and a fragment shader 1450. Variations of a graphics rendering pipeline may have different processing stages from this non-limiting embodiment. Each frame rendered by a real-time graphics engine uses the central processing unit (CPU) and the graphics processing unit (GPU). The CPU may prepare or gather the necessary data for the graphics rendering pipeline and issues commands (e.g., draw calls) that are processed by the GPU pipeline. Examples of application programming interfaces (APIs) that can be used by the real-time graphics engine to command the GPU include OpenGL, DirectX, and other suitable APIs. A draw call instructing the GPU on what to draw can be sent by the graphics engine. Upon receiving the draw call to display a mesh (e.g., the object shown in FIG. 9B), the GPU uses a vertex shader to transform the triangles/vertices of the mesh using projection matrices to provide an appropriate view 1410. Vertex shaders process each vertex to transform the vertex's 3D position to a 2-dimensional coordinate on the screen. Various properties of a virtual object that is being rendered may be manipulated by the vertex shader (e.g., coordinates or position, color and/or texture coordinates). The transformed vertices output by the vertex shader are then received by the next processing stage such as a tessellation shader 1420. The tessellation shader can subdivided a mesh into finer meshes to add detail, for example, in the case that the mesh is closer to the viewing angle or perspective within the virtual simulation. The output of the tessellation shader may be received by a next processing stage such as a geometry shader 1430. The geometry shader can receive as input a set of vertices that represent a primitive, e.g., lines and triangles, and transform the primitive into a new primitive as an output. The output from the geometry shader can be received by a rasterizer 1440. The rasterizer transforms a vector input graphic into a rasterized output image (e.g., pixels that form the image).

The mesh that is rendered according to a graphics rendering pipeline such as the one illustrated in FIG. 14 will require one or more draw calls. As a given draw call proceeds through the graphics rendering pipeline, the various settings specified by the draw call (e.g., mesh parameters, textures, etc.) determined how the mesh is rendered. These settings make up the GPU state. Any change to these settings can require a new draw call to be issued. An example of a change to the GPU state is a when the texture to be rendered is changed (e.g., multiple textures to be rendered on a mesh). Thus, when multiple textures must be rendered on the mesh of a virtual object, multiple draw calls are typically required since each texture will corresponds to a different CPU state. These draw calls can cause a bottleneck in the graphics rendering process. However, the present disclosure provides for the use of a texture atlas that enables multiple textures to be utilized in a single draw call. For example, all the textures corresponding to the tissue types present in a given mesh (or even multiple meshes) may be combined on a single texture atlas, and the UV coordinates of the mesh are specified to look up the appropriate texture/tissue type on the texture atlas. Accordingly, a single draw call can be used to process the GPU state including the mesh coordinates and associated UV coordinates and texture atlas data through the visual rendering pipeline in order to generate the rendered virtual object.

In the context of surgical simulation, these tissue types can include muscle, bone, cartilage, nerve fiber, blood vessel, fascia or connective tissue, or other tissues. The disclosed systems and methods that utilize texture mapping using UV coordinates provide a relatively simple way of delivering higher visual fidelity than can be achieved with current methods. In some embodiments, the systems and methods described herein enable the use of a voxel representation of complex multi-part solids that can be manipulated in real time. In some embodiments, the use of a single texture atlas to represent multiple materials preserves rendering speed as limiting the materials to one texture means only one draw call is needed. In some embodiments, using UV coordinates to represent an offset into that texture allows the use of computationally efficient tri-planar mapping while also providing multiple surface support.

High Frequency Haptic Surface Data

In some aspects, described herein are systems and methods for providing a virtual reality simulation (including mixed or augmented reality) with haptic feedback. In some embodiments, the virtual reality simulation comprises one or more three-dimensional objects that a user can interact within the virtual environment inside the simulation. In some embodiments, the systems and methods enable interactions between a user and the three-dimensional object. The interactions can include simulated tactile interactions including haptic feedback. Conventional haptic feedback systems include video game controllers that provide simple haptic feedback such as vibrations in response to an in-game event such as, for example, a collision in a racing game. However, in virtual reality simulations, there is a lack of sophisticated haptic feedback systems that correspond to the visual environment. For example, in the case of a virtual medical simulation, a user may need to perform simulated surgery on a virtual object such as an organ. This simulation may include cutting, peeling, or otherwise manipulating the virtual object. The simplistic haptic feedback systems currently available fail to provide haptic feedback with a high level of detail.

In some embodiments, in 3D simulations using haptics, a conventional approach to defining the shape of an object is to use polygons as an easily computable approximation. By definition these polygons can be flat and contain no surface detail of any kind. In some embodiments, in order to increase the level of detail of the haptic shape, it may be necessary to increase the number of polygons and thus the load on the processor in terms of vertex data processing and collision detection. In some instances, humans can detect variation in surface texture with sub micro-meter accuracy, and modelling objects in the simulation at this level of detail quickly reaches a limit above which an acceptable framerate cannot be maintained and thus it can be difficult or near impossible to deliver precise haptic reactions at a small scale using the conventional approach.

The present disclosure provides a unique technique of adding haptic detail to the flat surface of polygons via a two dimensional array of height offsets which can be authored as a grey-scale image using commonly available graphics tools. In some embodiments, the visual rendering technique of bump-mapping is applied to the haptic domain. In some embodiments, polygons are defined by vertices in standard graphics engines. In some embodiments, each vertex contains its position in 3D space along with storage space for a two dimensional coordinate, referencing a point within an image, otherwise known as UV coordinates. In some embodiments, the present disclosure enhances the haptic detail available, and with visual rendering the UV coordinates are used to enhance the appearance of the surface of the object.

For example, bump maps can be used to fake the appearance of 3D surface detail on a 2D surface. Creating a complex or jagged surface on a 3D object would require many polygons to create the complex or jagged appearance. However, a grayscale texture can be applied to the surface of a 2D object, and the visual render engine can be programmed to render the texture based on the grayscale values. For instance, the visual render engine can determine how much light to bounce off a vertex in the texture based on the bump map value, which approximates the 3D texture.

Accordingly, the 2D texture can visually appear to have a 3D texture without requiring additional polygons to be rendered in order to modify the surface geometry to produce the desired texture, thereby providing a more efficient graphical rendering process.

The present disclosure, in some embodiments, utilizes bump map data to provide haptic detail in the virtual simulations described herein. In some embodiments, the bump map data (e.g., texture information for the vertices in a virtual object) is input into a haptic render pipeline. Accordingly, although polygons are flat, when a user draws a haptic device across the surface of a polygon, bump map data is utilized to determine the type and/or intensity of the feedback rather than using the 3D mesh of the virtual object. This approach modifies a technique used in the visual render pipeline and repurposes it for the haptic render pipeline to provide an innovative solution to the technical problem of generating a virtual environment having haptic feedback that is both detailed and efficient.

Figure 11A:
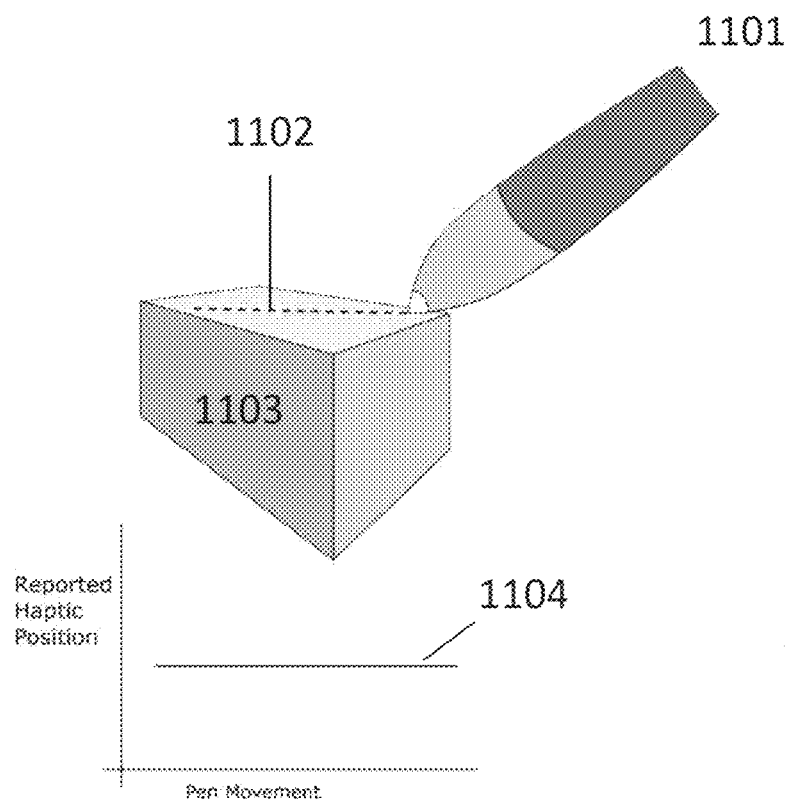
FIGS. 11A and 11B show a comparison of 3D simulations without and with high frequency data.
Figure 11B:
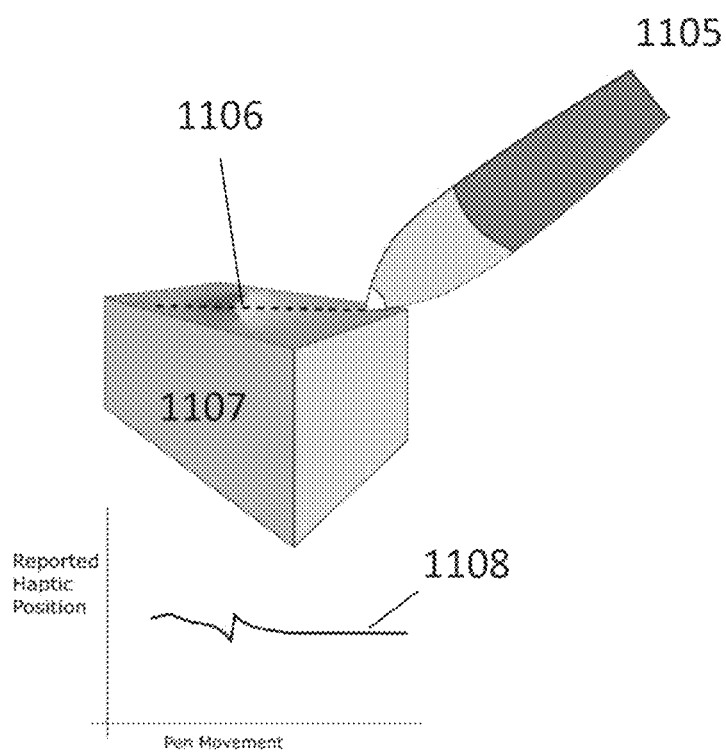

FIGS. 11A and 11B show a comparison of 3D simulations without and with high frequency data. FIG. 11A illustrates a standard appearance of a haptic object without high frequency haptic surface data. As shown, a virtual tool 1101 (in this case, a pen, but can be any physical hand-held component including those described herein and other known surgical or medical tools) is drawn across the surface 1102 of a virtual object 1103 (e.g., a 3D polygon having multiple faces or surfaces). In this case, there is no high frequency haptic surface data as indicated by the uniform surface 1102 of the area the tool is drawn across. Thus, the corresponding haptic position providing haptic feedback is a zero-slope straight line 1104. By contrast, FIG. 11B illustrates an enhanced appearance of surface detail on a haptic object due to application of high frequency haptic surface data by a visual rendering technique from the present disclosure. Whereas conventional graphics engines utilize UV coordinates to enhance the appearance of the surface of the object in a visual rendering pipeline, disclosed herein are systems, methods, and software that utilize visual data to provide haptic feedback through a haptic rendering pipeline. Accordingly, as shown in FIG. 11B, when the virtual tool 1105 is drawn across the surface 1106 of the simulated object 1107, the visual data (e.g., bump map) is used to provide haptic position 1108 corresponding to the tool's movement. As shown, the bump map data projected onto the surface 1106 shows darker and lighter portions corresponding to the varying bump map values at each position (e.g., vertex) on the surface 1106. These darker and lighter portions normally indicate how light is bounced off of the object in conventional bump mapping to produce a desired texture. For example, bump mapping can be used to give the appearance of changes in height on the surface of the object. However, in the case of certain haptic rendering processes described herein, the bump map values are used to indicate haptic feedback such as, for example, the height or texture of the surface of an object. Accordingly, as the tool 1105 is drawn across the surface 1106 of the object, the tool 1105 will contact areas of the surface 1106 that have varying bump map values. In this example, these bump map values are processed in a haptic rendering pipeline to provide dynamic haptic feedback as the tool moves across the surface. For example, FIG. 12 illustrates an embodiment of the system in which virtual object data 1260 can include bump map data that is integrated with haptic data 1250 (e.g., haptic feedback intensities and/or feedback that correspond to bump map values) by the haptic rendering pipeline 1280 in order to provide haptic feedback to the input device 1210 (e.g., hand-held component).

Figure 13:
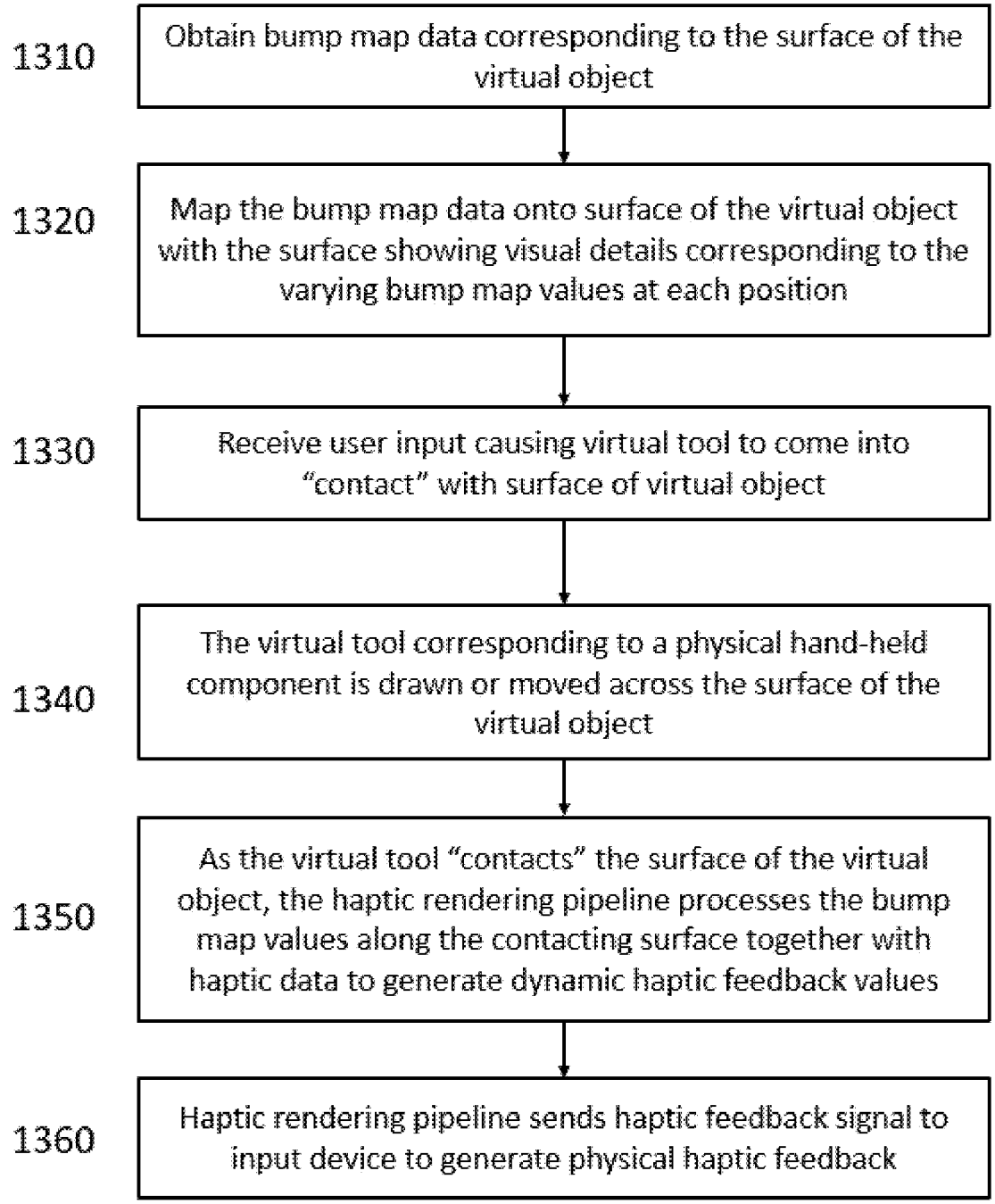
FIG. 13 shows an illustrative flow chart outlining steps for providing haptic feedback using bump mapping.

FIG. 13 shows an illustrative flow chart outlining steps for providing haptic feedback using bump mapping. Bump map data is corresponding to the surface of the virtual object is obtained 1310. The bump map data is mapped onto the surface of the virtual object with the surface having varying bump map values at the positions on the surface (e.g., vertex) 1320. User input is received through a movement or force exerted upon a hand-held component corresponding to a virtual tool, which causes the virtual tool to be brought into virtual "contact" with the surface of the virtual object 1330. As the user manipulates the hand-held component corresponding to a virtual tool, the virtual tool is drawn or moved across the surface 1340. As the virtual tool contacts the surface of the virtual object, the haptic rendering pipeline processes the bump map values along the contacting surface together with haptic data to generate dynamic haptic feedback 1350 (e.g., haptic feedback intensity is determined based on bump map values). Finally, the haptic rendering pipeline sends a haptic feedback signal to the hand-held component to generate a physical haptic feedback 1360 (e.g., changes in resistance corresponding to changes in "height" corresponding to the bump map values to simulate surface "bumpiness"). Accordingly, graphics rendering information (e.g., bump map or texture) is used or integrated into a haptic feedback rendering pipeline to enable high definition or high resolution haptic feedback. The haptic feedback can be the intensity and/or type of feedback, including at least the various haptic feedback examples described herein. The haptic feedback can be provided via the physical hand-held component. For example, a user may be holding a physical tool corresponding to a virtual scalpel and draws its tip (corresponding to the virtual blade) across the surface of a virtual arm to make an incision within a simulated surgical environment. The visual data such as bump map values may indicate a relatively low degree of resistance as haptic feedback since the tool is cutting simulated skin. Alternatively, when the user draws the virtual scalpel across bone, the resistance may be greatly increased and/or vary based on the more "bumpy" texture of the bone. In some cases, unevenness in the surface (e.g., a "bumpy" texture of a surface) can be simulated by varying the resistance as the virtual tool travels across the surface of the virtual object in accordance with the unevenness.

In some embodiments, the present disclosure opens up the ability to create unprecedented levels of surface detail on a haptic object allowing for the first time the haptic detail to match in resolution the visual detail available with modern 3D real time simulations. In some embodiments, the system, tool, and methods align haptic modelling techniques more closely with those commonly used in visual modelling, enabling any 3D artist to author haptic content using existing toolchains and without specialist knowledge or training. In some embodiments, the present disclosure opens up the possibility to use other common graphical techniques for giving surface detail and apply them to the haptic domain, such as UV scrolling to provide the impression of flow, bump map multiplication to give dynamic effects such as spatial areas of pulsing and other dynamic variations. Such a feat has never before been accomplished in the area of virtual simulations, which represents a tremendous improvement in this technical field. For example, the coupling of haptic detail to high resolution visual detail on the virtual objects can revolutionize high fidelity and detail simulations such as medical simulations in which the fine details are of critical importance for providing a realistic representation of the visual and tactile elements of a medical procedure. Accordingly, the visual or texture details on the surface of a virtual object (e.g., initial exterior surface and/or interior surface after the object has been "cut" open) can be incorporated into the haptic rendering process by converting the visual details into corresponding haptic details. For example, while bump map values of the object's surface may be used to indicate height or texture, these values may also be used to determine type or amount or intensity of haptic feedback for an interaction between a virtual tool and the object's surface. In addition to bump mapping, other texture mapping or simulating techniques can be used to determine haptic feedback. For example, standard texture mapping using UV wrapping of a premade texture onto a virtual object can provide texture information that is utilized to provide haptic feedback. Alternatively, the texture atlas techniques disclosed herein for providing efficient texture mapping may be used in combination with haptic feedback rendering pipeline that utilizes visual/texture data for haptic feedback. Other visual effects can also be achieved that correspond to haptic feedback effects. In the case of UV scrolling, the texture(s) on the virtual object can appear to dynamically change over time by adjusting or modifying the UV coordinates for the texture(s). For example, UV scrolling can be used to mimic the flow of water on a virtual river or lava flow. Such visual effects can also correspond to the dynamic change in haptic feedback.

In some embodiments, the systems and methods described herein generate a virtual simulation providing texture and/or haptic detail for one or more virtual objects while maintaining a frame-rate of at least about 20, 30, 40, 50, 60, 70, 80, 90, 100, 110, 120, 130, 140, 150, 160, 170, 180, 190, of at least 200 frames per second (FPS) or more. In some embodiments, the frame-rate is an average frame rate. In some embodiments, the frame-rate is a median frame rate. In some embodiments, an average frame-rate of at least about 90 fps is maintained. In some embodiments, the frame-rate is an average frame rate. In some embodiments, a frame-rate is a minimum frame rate.

In some embodiments, the systems and methods described herein generate a virtual simulation providing a frame-rate of at least about 20 to about 150. In some embodiments, the virtual simulation provides a frame-rate of at least about 20 to about 30, about 20 to about 40, about 20 to about 50, about 20 to about 60, about 20 to about 70, about 20 to about 80, about 20 to about 90, about 20 to about 100, about 20 to about 110, about 20 to about 120, about 20 to about 150, about 30 to about 40, about 30 to about 50, about 30 to about 60, about 30 to about 70, about 30 to about 80, about 30 to about 90, about 30 to about 100, about 30 to about 110, about 30 to about 120, about 30 to about 150, about 40 to about 50, about 40 to about 60, about 40 to about 70, about 40 to about 80, about 40 to about 90, about 40 to about 100, about 40 to about 110, about 40 to about 120, about 40 to about 150, about 50 to about 60, about 50 to about 70, about 50 to about 80, about 50 to about 90, about 50 to about 100, about 50 to about 110, about 50 to about 120, about 50 to about 150, about 60 to about 70, about 60 to about 80, about 60 to about 90, about 60 to about 100, about 60 to about 110, about 60 to about 120, about 60 to about 150, about 70 to about 80, about 70 to about 90, about 70 to about 100, about 70 to about 110, about 70 to about 120, about 70 to about 150, about 80 to about 90, about 80 to about 100, about 80 to about 110, about 80 to about 120, about 80 to about 150, about 90 to about 100, about 90 to about 110, about 90 to about 120, about 90 to about 150, about 100 to about 110, about 100 to about 120, about 100 to about 150, about 110 to about 120, about 110 to about 150, or about 120 to about 150. In some embodiments, the virtual simulation provides a frame-rate of at least about 20, about 30, about 40, about 50, about 60, about 70, about 80, about 90, about 100, about 110, about 120, or about 150. In some embodiments, the virtual simulation provides a frame-rate of at least at least about 20, about 30, about 40, about 50, about 60, about 70, about 80, about 90, about 100, about 110, or about 120. In some embodiments, the virtual simulation provides a frame-rate of at least at most about 30, about 40, about 50, about 60, about 70, about 80, about 90, about 100, about 110, about 120, or about 150.

In some embodiments, the frame rate is maintained when the virtual simulation comprises at least 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, 500, 600, 700, 800, 900, 1000, 2000, 3000, 4000, or 5000 or more virtual objects. In some embodiments, the one or more virtual objects have a high visual detail and/or high haptic detail. In some embodiments, high visual and/or high haptic detail refers to resolution in the millimeter range and/or the micron range. In some embodiments, the frame rate is at least 10%, at least 20%, at least 30%, at least 40%, at least 50%, at least 60%, at least 70%, at least 80%, at least 90%, or at least 100% higher than a frame rate generated using a conventional approach without use of a texture atlas for dynamic representations of virtual object(s) (assuming the same computing hardware is used in the comparison). In some embodiments, the frame rate is at least 2, 3, 4, 5, 6, 7, 8, 9, or 10 times higher than a frame rate generated using the conventional approach.

Certain Definitions

As used herein, the singular forms "a", "an" and "the" include plural references unless the context clearly dictates otherwise. For example, the term "a texture" includes a plurality of textures. Any reference to "or" herein is intended to encompass "and/or" unless otherwise stated.

Unless otherwise indicated, open terms for example "contain," "containing," "include," "including," and the like mean comprising.

As used herein, the term "about" a number refers to that number plus or minus 10% of that number. The term "about" a range refers to that range minus 10% of its lowest value and plus 10% of its greatest value. The lower and upper bounds for "about" a number are rounded up. For example, a frame-rate of about 105 indicates a frame-rate range of 95 to 116 (105−10.5 for 94.5 which is rounded up to 95; and 115+10.5 for 115.5 which is rounded up to 116).

As used herein, the phrases "at least one of a, b, c, and d" and "at least one of a, b, c, or d" refer to a, b, c, or d, and any and all combinations comprising two or more than two of a, b, c, and d.

As used herein, the term "XR" or "cross reality" refers to an augmented, virtual, and/or mixed reality environment and can encompass a wide range of hardware and software, including sensors, interfaces, software applications, and other tools useful for generating this reality. Wherever any one category of "XR" or "cross reality" is referenced herein (e.g., "augmented reality," "virtual reality," or "mixed reality"), the other forms of cross reality are also denoted. Thus, a reference to an augmented reality system would also indicate a virtual reality system and a mixed reality system as well as the broader category of a cross reality system.

As used herein, "virtual reality" refers to an interactive experience within a computer-simulated environment that engages one or more senses.

As used herein, "mixed reality" or "hybrid reality" refers to an interactive experience that merges both the real world environment and a virtual environment to produce a hybrid environment that combines sensory modalities from both the real and virtual such that physical and digital objects can be coexist and optionally interact.

As used herein, "augmented reality" refers to an interactive experience with the real world environment in which physical or otherwise real objects present in the real world environment are "augmented" with computer-generated sensory information such as visual, auditory, or haptic.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for providing a virtual reality or augmented reality surgical simulation comprising a virtual object comprising a plurality of voxels, said system comprising:
   (a) a processor;
   (b) a hand-held component operatively coupled to the processor; and
   (c) a non-transitory computer readable storage medium encoded with a computer program that causes the processor to:
      (i) identify a plurality of UV coordinates associated with the plurality of voxels of the virtual object, wherein the plurality of voxels are associated with tissue type data used to generate the plurality of UV coordinates;
      (ii) locate data comprising haptic information associated with the plurality of voxels, and a plurality of textures corresponding to the tissue type data associated with the plurality of voxels of the virtual object within a texture atlas, wherein each of the plurality of textures is located within the texture atlas using an offset value that is based on at least one UV coordinate associated with at least one voxel of the plurality of voxels;
      (iii) map the data comprising the plurality of textures onto the plurality of voxels of the virtual object;
      (iv) display the virtual object comprising the plurality of textures mapped onto the plurality of voxels within the surgical simulation;
      (v) provide haptic feedback to a user through the handheld component, wherein the haptic feedback corresponds, in part, to bump map data corresponding to a surface of the virtual object; and
      (vi) display, when a force is transmitted to the virtual object through the hand-held controller, a response of a texture associated with the virtual object to the force.

2. The system of claim 1, wherein the hand-held component comprises a wand, a joystick, a mouse, a roller, a grasper, or a glove, wherein the hand-held component controls a virtual surgical instrument within the virtual or augmented reality surgical simulation, and wherein the virtual surgical instrument comprises a scalpel, a needle driver, a clamp, a clip applier, a surgical stapler, a retractor, a periosteal elevator, a rongeur, a nerve hook, a curette, an awl, a probe, a sagittal saw, a drill, a suture, a hammer, a finger, a laparoscopic instrument, an electrocautery, a suctioning instrument, or any combination thereof.

3. The system of claim 2, wherein the computer program further causes the processor to display a movement of the virtual surgical instrument in the surgical field in the same direction as a movement of the hand-held component based on the input.

4. The system of claim 1, wherein the virtual reality or augmented reality surgical simulation comprises a representation of at least one of a bone, a muscle, an organ, a blood vessel, blood, and a nerve.

5. The system of claim 1, wherein all textures that are mapped within the surgical simulation are positioned on the texture atlas and each mapped texture is associated with a set of unique UV coordinates.

6. The system of claim 1, wherein the computer program further causes the processor to display a seamless movement of a texture within the virtual reality or augmented reality surgical simulation.

7. The system of claim 1, wherein the computer program further causes the processor to display both an exterior texture and an interior texture of the virtual object when that virtual object is cut or altered to expose the interior texture with a virtual surgical instrument within the surgical simulation, and wherein the exterior texture and the interior texture are positioned on the texture atlas and each have a unique location within the texture atlas associated with unique UV coordinates.

8. The system of claim 7, wherein the computer program further causes the processor to simultaneously display the exterior texture and the interior texture and wherein the processor draws upon the texture atlas once.

9. The system of claim 1, wherein the haptic feedback comprises a sensation that represents the response of the texture to the force.

10. The system of claim 1, wherein the virtual object is rendered for display as a three-dimensional mesh generated from the plurality of voxels.

11. The system of claim 10, wherein the plurality of textures is mapped onto the three-dimensional mesh using a triplanar shader.

12. The system of claim 10, wherein the three-dimensional mesh is generated using an adaptive mesh algorithm.

13. The system of claim 12, wherein the adaptive mesh algorithm is a marching cubes or tetrahedrons algorithm.

14. The system of claim 1, wherein surgical simulation comprises two or more virtual objects.

15. The system of claim 1, wherein the virtual object is a simulated patient or an anatomic portion of the simulated patient.

16. The system of claim 15, wherein the anatomic portion of the simulated patient comprises an arm, a leg, a torso, a head, or neck.

* * * * *